United States Patent
Pezzotti

(10) Patent No.: US 8,211,707 B2
(45) Date of Patent: Jul. 3, 2012

(54) STRESS MEASURING DEVICE

(76) Inventor: Giuseppe Pezzotti, Kyoto (JP)

( * ) Notice: Subject to any disclaimer, the term of this patent is extended or adjusted under 35 U.S.C. 154(b) by 1915 days.

(21) Appl. No.: 10/507,258

(22) PCT Filed: Mar. 13, 2003

(86) PCT No.: PCT/JP03/03037
§ 371 (c)(1),
(2), (4) Date: Sep. 10, 2004

(87) PCT Pub. No.: WO03/076888
PCT Pub. Date: Sep. 18, 2003

(65) Prior Publication Data
US 2005/0130316 A1    Jun. 16, 2005

(30) Foreign Application Priority Data
Mar. 14, 2002   (JP) ................. P2002-070932

(51) Int. Cl.
G01N 21/62 (2006.01)
(52) U.S. Cl. ........................................ 436/171
(58) Field of Classification Search .................. 436/171; 422/171
See application file for complete search history.

(56) References Cited

U.S. PATENT DOCUMENTS

| | | | |
|---|---|---|---|
| 4,774,150 A * | 9/1988 | Amano et al. | 428/690 |
| 5,278,408 A * | 1/1994 | Kakibayashi et al. | 250/311 |
| 5,350,921 A * | 9/1994 | Aoyama et al. | 250/311 |
| 5,552,602 A * | 9/1996 | Kakibayashi et al. | 250/311 |
| 2001/0017059 A1* | 8/2001 | Xu et al. | 73/800 |

FOREIGN PATENT DOCUMENTS

| | | |
|---|---|---|
| JP | 58-158847 | 9/1983 |
| JP | 6-10612 | 2/1994 |
| JP | 07-012763 | 1/1995 |
| JP | 07-019969 | 1/1995 |
| JP | 11-237216 | 8/1999 |
| JP | 11-295159 | 10/1999 |
| WO | WO 00/39523 | 7/2000 |

OTHER PUBLICATIONS

Galiotis, C.; Paipetis, A.; Marston, C. "Unification of Fibre/Matrix Interfacial Measurements with Ramam Microscopy." J. Raman Spectrosc., 1999, 30, pp. 899-912.*

Schlichting, K. W.; Vaidyanathan, K. Sohn, Y.H.; Jordan, E.H.; Gell, M.; Padture, N.P. "Application of Cr3+ photoluminescence piezo-spectroscopy to plasma-sprayed thermal barrier coatings for residual stress measurement." Materials Science and Engineering A 291, 2000. pp. 68-77.*

(Continued)

Primary Examiner — Bobby Ramdhanie
(74) Attorney, Agent, or Firm — Stites & Harbison PLLC; Douglas E. Jackson

(57) ABSTRACT

The stress measuring method of the present claimed invention includes an external force impressing process that applies an external force to a specimen, an electron beam irradiating process that irradiates an electron beam to the specimen, a spectroscopy process that conducts spectroscopy on light generated from the specimen by the above-mentioned electron beam irradiating process so as to obtain a spectrum, and a stress calculating process that obtains a stress based on a spectrum shift between a specimen spectrum obtained by irradiating the electron beam on the above-mentioned specimen and a stress impressed spectrum obtained by irradiating the electron beam on the specimen in a state that a stress exists due to the above-mentioned external impressing process.

21 Claims, 16 Drawing Sheets

OTHER PUBLICATIONS

Muraki, K.G.; Sergo, V.; Pezzotti, G.; Nishida, T. "Mapping of residual stresses around an indentation in b-Si3N4 using Raman Spectroscopy." Journal of Materials Science, 1997, pp. 5419-5423.*

Yoshikawa,M.; Maegawa, M.; Katagiri, G.; Ishida, H. "Characterization of anisotropic stress around Si trenches by polarized Raman spectroscopy." J. Appl. Phys. 78 (2), 1995. pp. 941-944.*

Muraki, N.; Matoba, N.; Hirano, T.; Yoshikawa, M. "Determination of thermal stress distribution in a model microelectronic device encapsulated with alumina filled epoxy resin using fluorescence spectroscopy." Polymer, 43, 2002, pp. 1277-1285.*

Pezzotti, G. "In situ Study of Fracture Mechanisms in Advanced Ceramics using Fluorescence and Raman Microprobe Spectroscopy." J. Raman Spectrosc. 1999, 30, pp. 867-875.*

* cited by examiner

US 8,211,707 B2

STRESS MEASURING DEVICE

FIELD OF THE ART

This invention relates to a stress measuring method and a stress measuring device for measuring stress of a specimen by irradiating electroluminescence, namely an electron beam on the specimen by the use of a luminescent phenomenon from the specimen.

BACKGROUND ART

A stress measuring method and a stress measuring device by the use of photoluminescence such as a Raman spectroscopy have been well known. The spectroscopy by the use of photoluminescence, namely, a photoluminescence spectroscopy has a resolution in units of μm and is used for measuring a stress or the like in an elastic material.

A stress measuring method and a stress measuring device by the use of the Raman spectroscopy are open to public, for example, in an official gazette of Japan Patent Laid-open Number 7-19969, Japan Patent Laid-open Number 6-347343, and Japan Patent Laid-open Number 8-5471.

A stress measuring method comprising a laser luminous source, an objective lens for narrowing down the laser light in a shape of a spot on a surface of an object whose stress is to be measured, a half mirror for introducing the scattered light into a spectrometer, and a spectroscopy is open to public in the above official gazettes.

However, the stress measuring by the use of the above Raman spectroscopy has a problem such that a positional resolution is low.

More specifically, there is a limit to narrowing down a diameter of a beam spot of the laser light when the light is irradiated on a specimen for the stress measuring method by the use of the above Raman spectroscopy. For example, the positional resolution of the stress measuring method by the use of the Raman spectroscopy is about 1 μm and the positional resolution of the stress measuring method by the use of proximity field light is about 200 nm.

Recently, a new material is manufactured such as a nanotube or a nanocoil having a minute structure wherein atoms/molecules are arranged in a level of nano-technology. Since the conventional stress measuring method by the use of the Raman spectroscopy can not narrow down a beam spot diameter and is low in a positional resolution, in case of measuring a stress of the new material in the level of nano-technology (for example, about several nm) wherein a recurring unit size of the new material is mostly not over 200 nm, the stress of a local portion (nano level) can not be measured because an average stress of whole of the beam spot area is obtained.

As a result of this, in case that a high stress concentration is applied to an extremely small area, for example, in nano level, the stress concentration can not be detected because the stress is measured on a basis of an average value, resulting in failure in determining a cause of break-down.

Especially in a field of a stress measurement, increasing the positional resolution contributes to not only improving an accuracy of localization but also enabling measurement of high stress concentration on a local area that has not been measured by a conventional method, which will make a rapid progress in clearing up a cause of break-down or measuring physicality.

Furthermore, stress sensitivity tends to be low and it is difficult to measure a minute stress change in the conventional stress measuring method by the use of the Raman spectroscopy.

The present claimed invention intends to provide a stress measuring method and a stress measuring device high in a positional resolution and superior in stress sensitivity.

DISCLOURE OF THE INVENTION

In order to solve the above-mentioned problems, the stress measuring method in accordance with the present claimed invention is characterized by comprising an electron beam irradiating process that irradiates an electron beam on a specimen, a spectroscopy process that analyses light generated from the specimen in the above-mentioned electron beam irradiating process and obtains a spectrum, and a stress calculating process that obtains a stress change based on a spectrum shift between a spectrum obtained from the specimen in a predetermined state and a spectrum obtained from the specimen in a state different from the predetermined state. "A state different from the predetermined state" includes a case that only a measuring place is different for the identical specimen.

As a concrete embodiment, it is represented that a residual stress is obtained in the stress calculating process based on a spectrum shift between a specimen spectrum as being a spectrum in a state that no stress exists in the specimen and a stress impressed spectrum as being a spectrum in a state that a residual stress exists in the specimen.

In addition, the stress measuring method of this invention may have an arrangement that an external force impressing process that applies an external force to the specimen prior to the above-mentioned electron beam irradiating process is further included, and an internal stress is obtained from a spectrum shift between an internal stress impressed spectrum as being a spectrum in a state that an internal stress is generated in the specimen by the external force impressing process and a specimen spectrum as being a spectrum in a state that no stress exists in the specimen or a stress impressed spectrum as being a spectrum in a state that a residual stress exists in the specimen.

"Stress" to be measured by the stress measuring method of this invention indicates an internal stress and/or a residual stress.

The above-mentioned specimen spectrum indicates a spectrum in a state that no stress exists in the specimen. In addition, the stress impressed spectrum indicates a spectrum in a state that a residual stress exist in the specimen. The internal stress impressed spectrum indicates a spectrum in a state that an external force is applied to the specimen. In addition, "the external force" indicates energy (force, heat or the like) applied from outside of the specimen.

An electron is excited between energy levels such as, for example, between the highest occupied level (HOMO) and the lowest vacant level (LUMO) by irradiating an electron beam having a specific wavelength. The excited electron emits light (including fluorescence) when restored to a normal state. The light emission includes structural and analytical information on the specimen.

In case that a stress exists in the specimen, a position of a spectrum is shifted (a spectrum shift) if the specimen spectrum and the stress impressed spectrum are compared. More concretely, if a stress applied to the specimen changes, an interatomic distance (an interionic distance) constituting the specimen changes. As a result of this, an electronic state of an atomic element (an ion) changes, thereby changing an electronic state of the electron. Then a position of a spectrum of the specimen in a state that an external force is applied to the specimen differs from a position of a spectrum of the specimen in a state that no external force is applied to the specimen, therefore a spectrum of the internal stress impressed spectrum is shifted from a spectrum of the specimen spectrum.

In addition, for example, in case of an amorphous material such as glass, if the amorphous material is heated (an external force is applied) so as to be melted, followed by rapid cooling, the amorphous material is distorted due to a difference of coefficient of thermal expansion. This distortion generally remains inside the material without being resolved. The state that inside distortion exists means a state that a residual stress exists. A spectrum shift is produced between a place where the above-mentioned residual stress exists and a place where no residual stress exists.

As a result, the residual stress applied to the specimen can be obtained from a difference between a position of the stress impressed spectrum and a position of the specimen spectrum. In addition, for example, a size of an internal force generated by an external force (force, heat) applied to the specimen can be obtained from a spectrum shift between a spectrum in a state that no external force is applied and a spectrum in a state that an external force is applied. In this case, the same residual stress has to exist in both of the spectra.

As mentioned above, the stress measuring method in accordance with the invention measures a stress by the use of light generated by irradiating an electron beam on a specimen. More concretely, in order to measure a residual stress, a stress is calculated from a spectrum shift between a specimen spectrum in a state that no stress exists in the specimen and a stress impressed spectrum in a state that a residual stress exists in the specimen. In addition, in order to measure an internal stress generated in the specimen by the above-mentioned external force impressing process, a stress is calculated from a difference between an internal stress impressed spectrum in a state that an external force is impressed and the above-mentioned stress impressed spectrum or a specimen spectrum.

Since a wavelength of the above-mentioned electron beam is shorter than, for example, laser light that has been used for a conventional stress measuring method, a beam spot diameter (a diameter of a beam spot) of the electron beam can be made small. As a result, an arrangement (electroluminescence spectroscopy) for measuring a stress by the use of light generated by irradiating an electron beam on a specimen can measure a stress with a superior positional resolution (a space resolution) compared with a conventional arrangement (photoluminescence spectroscopy) for measuring a stress by the use of light generated by irradiating light on a specimen. More concretely, in case of using an electron beam, since a beam spot diameter can be made small to an extent of not greater than 100 nm, more preferably not greater than 10 nm, furthermore preferably not greater than 2 nm, the most preferably 0.13 nm, a stress can be measured with an extremely high positional resolution compared with a conventional arrangement.

As a result, since a stress can be measured with a high positional resolution (several nm unit), a stress analysis regarding to, for example, a microscopic portion such as a carbon nano tube and a micro machine can be conducted that has not been conducted by the use of the conventional arrangement. In addition, a structure of a specimen can be estimated based on the calculated stress.

Furthermore, it is possible for the arrangement for measuring a stress by the use of light emission obtained by irradiating an electron beam on a specimen to enlarge a spectrum shift as proven experimentally compared with the conventional arrangement wherein laser light is irradiated. As a result, since a spectrum shift can be measured more accurately, a measurement of a sensitive stress, namely a minute stress change that could not be measured by the conventional arrangement, can be conducted.

It is required that this invention that has a high space resolution and that can measure a minute stress change should specify a specimen spectrum in a state that no stress exists, namely 0 point spectrum, in order to guarantee functions such as a high space resolution and measurement of minute stress change.

As a preferable method to specify the above-mentioned specimen spectrum, it is represented that the above-mentioned electron beam irradiating process includes a broad area electron beam irradiating process that irradiates an electron beam without narrowing down on a broad area that is broad enough compared with a spot size of an electron beam that is narrowed down to obtain a requested space resolution, and a spectrum obtained by analyzing light generated from the specimen in the broad area electron beam irradiating process is made to be a specimen spectrum as being a spectrum in a state that no stress exists in the specimen in the stress calculating process.

In addition, the above-mentioned electron beam irradiating process may include a broad area electron beam irradiating process that irradiates an electron beam with scanning a spot size on a broad area that is broad enough compared with the spot size of an electron beam that is narrowed down to obtain a requested space resolution, and an average of a spectra of light generated by irradiating each electron beam in the broad area electron beam irradiating process is made to be the specimen spectrum as being the spectrum in a state that no stress exists in the specimen in the stress calculating process.

Preferably, if the above-mentioned broad area is the entire area of the specimen, the specimen spectrum can be specified more steadily. In addition, if a diameter of the above-mentioned broad area is set as not less than 100 times of the spot size of the electron beam, the specimen spectrum can be specified with accuracy.

As another different method to obtain the specimen spectrum, it is represented that a minute amount sample obtaining process that obtains a minute amount of a sample from the specimen is further included, and a spectrum of light obtained by irradiating an electron beam on the minute amount of the sample is made to be the specimen spectrum as being the spectrum in a state that no stress exists in the specimen in the stress calculating process. In order to obtain a minute amount of a sample, it is preferable as a matter of convenience for measurement that a minute amount sample obtaining means such as, for example, a nano manipulator or the like is used and the minute amount of the sample can be obtained under the same environment as that of the electron beam irradiation. "Minute amount" is an amount of an extent that a stress such as a residual stress can not exist, and it is a matter of course that the amount varies depending on a shape of the minute amount of the sample.

For example, in case that the specimen is a semiconductor or the like, composition of the specimen may vary partially due to proliferation of doped impurities. In this case, since a chemical shift is generated due to a difference of the composition, the chemical shift must be considered, otherwise an error will be generated to the specimen spectrum.

In order to prevent this, it is preferable that a composition analyzing process that analyzes a partial difference of composition of the specimen is further included, and in the above-mentioned stress calculating process the above-mentioned specimen spectrum is determined for each area where composition of the specimen differs obtained by the above-mentioned composition analyzing process in consideration of a spectrum shift generated due to the difference of composition.

It is more preferable that the stress measuring method of this invention has an arrangement wherein external light whose spectrum is known is irradiated in the above-mentioned electron beam irradiating process, a spectrum of the external light and a spectrum of light emission from the specimen are obtained in the above-mentioned spectroscopy process, and each position of spectra from the specimen in each state to be compared in order to measure a stress change is compensated based on the spectrum of the external light in the above-mentioned stress calculating process.

More concretely, the arrangement is represented in that each of a position of the specimen spectrum and a position of the stress impressed spectrum is compensated based on the spectrum of the external light, or that each of a position of the internal stress impressed spectrum and a position of the specimen spectrum or a position of the stress impressed spectrum is compensated based on the spectrum of the external light.

In this case, it is preferable that a predetermined peak wavelength as being a reference for the above-mentioned external light spectrum is set near a predetermined peak wavelength for the light emission spectrum from the specimen, more concretely set within generally twice as much as a half value width of the above-mentioned peak wavelength. This is because a measurement range can be secured.

The above-mentioned external light indicates light that is irrelevant to light emission from the specimen and whose spectrum is known. In accordance with the above-mentioned arrangement, a position of the spectrum of the specimen spectrum and a position of the spectrum of the stress impressed spectrum are compensated based on a spectrum of the external light. More concretely, spectroscopy is conducted also on an external light in conjunction with obtaining each spectrum. On an occasion of calculating a spectrum shift between a specimen spectrum and a stress impressed spectrum, if a position of a spectrum of the external light included in the specimen spectrum coincides with a position of a spectrum of the external light included in the stress impressed spectrum, an error can be minimized resulting from a measurement environment, thereby calculating the spectrum shift more accurately. In addition, spectra measured by different measuring devices can also be compared. This can be applied also to the internal stress impressed spectrum, the above-mentioned specimen spectrum or the stress impressed spectrum.

It is preferable that the stress measuring method of this invention has an arrangement further including a correlation calculating process that calculates a correlation between an amount of external force impressed on the specimen and an amount of the above-mentioned spectrum shift.

There is a correlation between an amount of external force impressed on a specimen and the above-mentioned spectrum shift. More concretely, a relationship between an amount of external force impressed on a specimen and the above-mentioned spectrum shift is a linear function (proportional) to an extent of several GPa. A stress (an internal stress, a residual stress) applied to a specimen can be calculated by the use of this correlation. More concretely, in case of measuring a residual stress of a specimen, a spectrum of a specimen in a state that a residual stress exists in the specimen is measured, a spectrum of the specimen in a state that the residual stress is removed from the specimen, and then a difference (a peak shift) between the two spectra is measured. Then the peak shift is applied to the above-mentioned correlation and a residual stress remaining in the above-mentioned specimen can be calculated.

In accordance with the above-mentioned arrangement, since the correlation calculating process that calculates a correlation between an amount of external force impressed on a specimen and an amount of the above-mentioned spectrum shift is included, a stress (an internal stress, a residual stress) applied to the specimen can be calculated even though a correlation between the amount of the external force impressed on the specimen and the amount of the above-mentioned spectrum shift is unknown.

It is more preferable that the stress measuring method has an arrangement that the above-mentioned specimen includes at least one kind of an element selected from a family consisting of lanthanoid by an amount within a range of 1 ppm~10000 ppm.

In case that light emission can not be obtained from the specimen by irradiating an electron beam on the specimen, a stress can not be measured. As a result, a light-emitting material (a fluorescent material) has to be included (doped) into the specimen if light emission can not be obtained from the specimen.

The lanthanoid is a transition element wherein 4f electrons are filled in sequentially in an arrangement of an electron. The lanthanoid is a light emitting material wherein 4f-4f transition easily happens. Then light emission specific to the lanthanoid can be obtained if an element of the lanthanoid is included in the specimen. In accordance with the above-mentioned arrangement, since the specimen includes lanthanoid by an amount within a range of 1 ppm~10000 ppm, it is possible for a specimen that does not emit light (fluorescence) to measure light emitted due to 4f-4f transition of lanthanoid if the specimen is doped with at least one element selected from a family consisting of the lanthanoid, which makes it possible to measure a stress.

In addition, since the lanthanoid can obtain a clear spectrum in spite of a very little amount, a ratio of the element to the specimen is preferably an extremely small amount (within a range of 1 ppm~10000 ppm, more preferably within a range of 50 ppm~10000 ppm, and furthermore preferably within a range of 100 ppm~10000 ppm). As a result, it is possible to measure a stress without changing a property (physicality) of the specimen.

It is preferable that the stress measuring method of this invention has an arrangement wherein the above-mentioned lanthanoid is at least one element selected from a family consisting of Sm, Eu, Tb, Y, La, Er, and Gd.

In accordance with the above-mentioned arrangement, since Sm, Eu, Tb, Y, La, Er, and Gd are higher in emission efficient compared with other element of the lanthanoid, an amount of the element to dope can be lessened. As a result, it is possible to measure a stress without changing a physicality of the specimen more securely.

In order to solve the above-mentioned problem, the stress measuring device of this invention is characterized by comprising an electron beam irradiating means that irradiates an electron beam on a specimen, a spectroscopy means that analyzes light generated from the specimen in the electron beam irradiating means so as to obtain a spectrum, and a stress calculating means that obtains a stress change generated in the specimen based on a spectrum shift between a spectrum obtained from the specimen in a predetermined state and a spectrum obtained from the specimen in a state different from the predetermined state.

The above-mentioned electron beam irradiating means is to irradiate an electron beam on a specimen and represented by, for example, an electronic microscope. The above-mentioned electron beam irradiating means includes a condenser lens or the like to narrow down a spot size of an electron beam.

In addition, the above-mentioned spectroscopy means is to obtain a spectrum by detecting light generated by an electron beam irradiating on a specimen by means of a detector and by separating the detected light into monochromatic light by means of a spectroscope. Concretely, a photo-multiplier tube (PMT) or the like is represented as the detector. In addition, a monochrometer or the like is represented as the above-mentioned spectroscopy.

Furthermore, the above-mentioned stress calculating means is to calculate a stress by analyzing a difference (a spectrum shift) between a specimen spectrum in a state that no external force is applied to the specimen and a stress impressed spectrum in a state that a stress exists in the specimen. The above-mentioned stress calculating means includes a program to obtain a stress by specifying the obtained spectrum by the use of a predetermined function and calculating a spectrum shift between a spectrum in a state that no stress exists and a spectrum in a state that a stress exists based on the specified spectrum. The above-mentioned state that a stress exists and the state that no stress exists vary depending on a stress (an internal stress, a residual stress) to be measured. More concretely, in case of measuring an internal stress, a spectrum shift is calculated between an internal stress impressed spectrum in a state that an internal stress exists and a specimen spectrum or a stress impressed spectrum in a state that no internal stress exists. In addition in case of measuring a residual stress, a spectrum shift is calculated between a stress impressed spectrum in a state that a residual stress exists and a specimen spectrum in a state that no residual stress exists.

In accordance with the above-mentioned arrangement, a stress is measured based on the emitted light from the specimen by irradiating an electron beam on the specimen. It is possible for the electron beam to narrow down a beam spot diameter compared with a conventional arrangement wherein laser light is irradiated on a specimen.

As a result, it is possible for an arrangement for measuring a stress by the use of light generated by irradiating an electron beam on a specimen to measure a stress that is superior in a positional resolution compared with a conventional arrangement for measuring a stress by the use of light generated by irradiating conventional light. More concretely, in case of using an electron beam, since a diameter of a beam spot can be made small not more than 100 nm, more preferably not more than 10 nm, furthermore preferably not more than 2 nm, the most preferably to an extent of 0.13 nm, it is possible to measure a stress whose positional resolution is extremely high compared with the conventional arrangement. As a result, it is possible to provide a stress measuring device whose positional resolution is high compared with a conventional stress measuring device.

It is preferable that the stress measuring device of this invention further comprises an external impressing means that impresses an external force on a specimen.

The above-mentioned external force impressing means is to apply an external force to a specimen. Concretely a jig or the like is represented as the above-mentioned external force impressing means. The jig can apply an external force such as compressing, pulling, bending or the like to a specimen. In addition, the jig can change a size of the external force continuously. A heating rapid cooling system to generate a residual stress in a specimen is also included in the external force impressing means.

In accordance with the above-mentioned arrangement, since the external force impressing means is provided, it is possible to measure an internal stress generated in a condition that the external force is applied to the specimen. In addition, since a size of the external force can be changed continuously, it is possible to measure a change of an internal stress applied to the specimen.

Furthermore, since the stress applied to the specimen can be measured in conjunction with a change of an external stress, for example, a molecular rearrangement of a macromolecule material can be monitored. In addition, if an amount of an external force impressed on the specimen is recorded, a correlation between a spectrum shift and the external force can be obtained.

It is more preferable that the stress measuring device of this invention has an arrangement of further comprising an external light irradiating means that irradiates external light whose spectrum is known.

The above-mentioned external light irradiating means is to emit light having a predetermined wave length, more specifically, a halogen light (a neon light) or the like. Since the halogen light emits light having a predetermined wave length, the obtained spectrum includes a peak as being a reference when spectroscopy is conducted on light from the halogen light in conjunction with the light emission obtained by irradiating an electron beam on a specimen in measuring the stress. It is possible to measure a stress accurately at any time by conducting compensation on each spectrum (a specimen spectrum, a stress impressed spectrum and an internal stress impressed spectrum) based on the peak of the spectrum as being the reference. Especially, in case of mapping a stress to display a stress distribution by measuring the stress of the specimen along a direction of a surface of the specimen, it is possible to compensate the stress by means of a reference point.

It is more preferable that the stress measuring device of this invention has an arrangement of further comprising a visualizing means that visualizes a portion to be measured of the above-mentioned specimen.

The above-mentioned visualizing means is to specify a position of a measuring portion and to display the measuring portion where a stress is to be measured on, for example, a CRT or the like. More concretely, the visualizing means is represented by an optical microscope or an electronic microscope.

In accordance with the above-mentioned arrangement, since the visualizing means is provided, it is possible to display a portion to be measured on the specimen with accuracy. As a result, it is possible to effectively measure a stress of, for example, the same portion.

It is more preferable that the stress measuring device of this invention has an arrangement wherein a diameter of a beam spot of an electron beam irradiated by the above-mentioned electron beam irradiating means is not more than 100 nm.

In accordance with the above-mentioned arrangement, if the diameter of the beam spot is made not more than 10 nm, furthermore preferably not more than 2 nm, the most preferably to an extent of 0.13 nm, it is possible to measure a stress whose positional resolution is extremely high compared with the conventional arrangement.

It is preferable that the stress measuring device of this invention has an arrangement wherein the above-mentioned electron beam irradiating means is a scanning electron microscope.

The scanning electron microscope is available in the market and it is possible to realize a stress measuring device with ease by the use of the scanning electron microscope.

BEST MODES OF EMBODYING THE INVENTION

Figure 1:
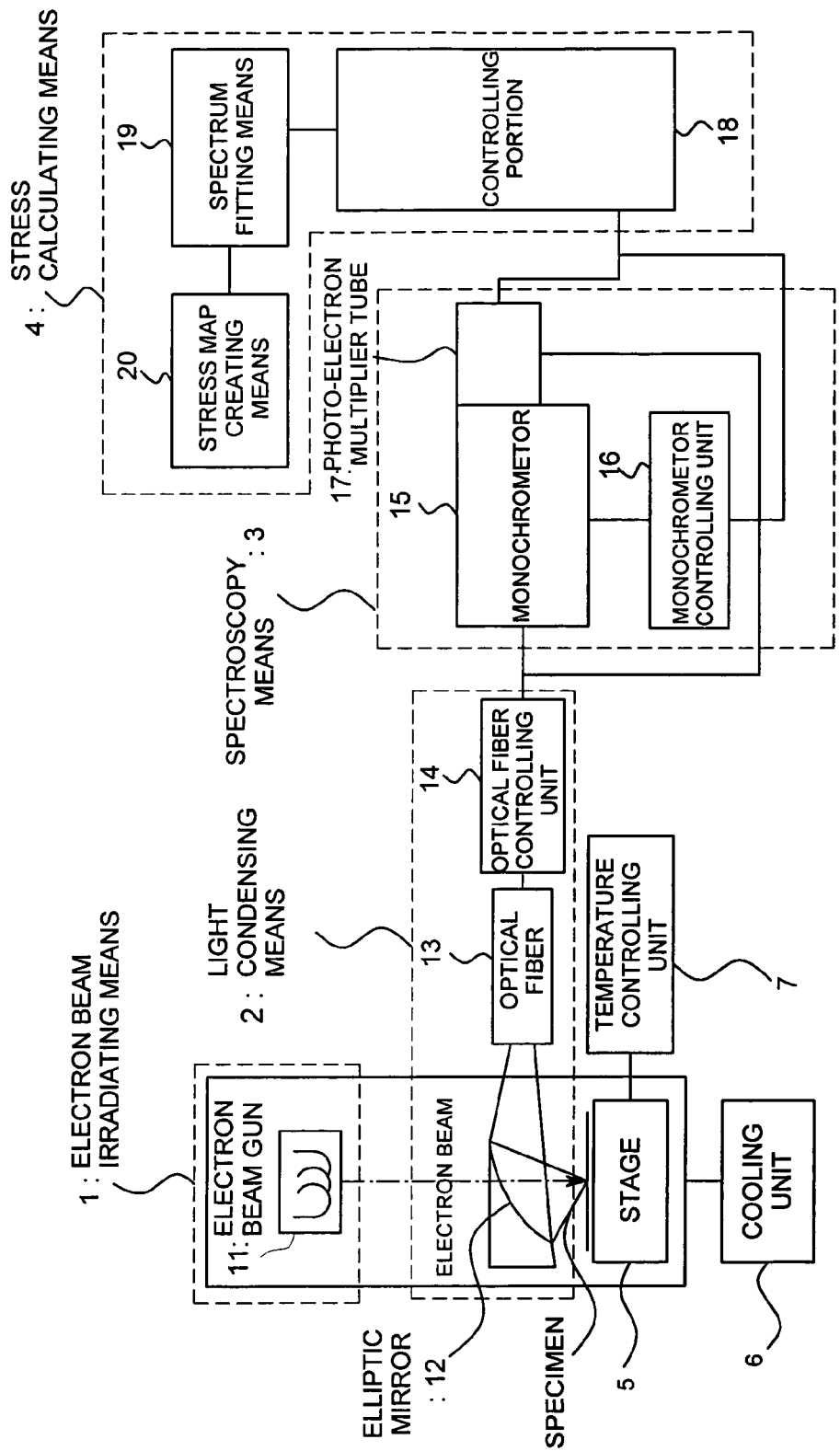
FIG. 1 is a block diagram showing an outline of a stress measuring device in accordance with one embodiment of the present claimed invention.

Following is an explanation of one embodiment of the present claimed invention based on FIG. 1 through FIG. 7.

A stress measured in this embodiment is an internal stress and/or a residual stress.

A specimen spectrum in the following explanation is a spectrum wherein no residual stress exists in the specimen. In addition, a stress impressed spectrum is a spectrum wherein a residual stress exists in the specimen. An internal stress impressed spectrum is a spectrum wherein an external force is applied to the specimen. "The external force" is energy (force, heat) applied from outside of the specimen, in other words, an external stress.

The above-mentioned internal stress is a stress generated in the specimen in a condition wherein a force or heat (external force) is applied to the specimen from outside. In case that the specimen is, for example, in a special shape or made of an amorphous material such as glass whose structure is not fixed, an external force applied to the specimen is not always equal to an internal stress generated in the specimen due to the external force. In addition, even though a predetermined external force is applied, the external force is not applied to the specimen uniformly, thereby varying a value of the internal stress by a section of the specimen.

The above-mentioned residual stress is a stress existing inside the specimen in a state that a force or heat is applied to the specimen from outside. More concretely, the residual stress is a stress remaining inside, for example, polycrystal that has been elastically transformed to be distorted by an external force and then the external force is removed. In addition, in case of an amorphous material such as glass, a residual stress generates due to a difference of coefficient of thermal expansion when the amorphous material is heated so as to be melted, followed by rapid cooling.

A stress measuring device in accordance with this embodiment comprises an electron beam irradiating means that irradiates an electron beam on the specimen, a spectral means that conducts spectroscopy on light generated from the specimen by the electron beam irradiating means so as to obtain a spectrum, and a stress calculating means that calculates a stress from a spectrum shift between a specimen spectrum wherein no stress exists in the specimen and a stress impressed spectrum wherein a stress exists in the specimen.

(Specimen to be Measured)

A specimen to be measured by the stress measuring device in accordance with the embodiment will be explained.

In accordance with the stress measuring device of the present claimed invention, a stress is measured by the use of light emission from the specimen due to an electron beam irradiated on the specimen. As a result, in order to measure a stress by the use of the stress measuring device of the present claimed invention, it is required to obtain light emission from the specimen due to an electron beam irradiated on the specimen.

As a specimen to be measured, a material that radiates light (including fluorescence) by itself due to an electron beam irradiated on the material is preferable. For example, light emission due to $Cr^{3+}$ in ruby (principal component; alumina) is represented as the material that radiates light by itself due to an electron beam irradiated on the material. In order to measure a stress of a specimen that does not radiate light by itself in spite of an electron beam irradiated on the specimen, more than one kind of an element (hereinafter called as a light-emitting material) selected from a family consisting of the lanthanoid series may be included in the specimen, namely, the above-mentioned light-emitting material may be doped on the specimen. This makes it possible to measure a stress by making use of light emission from the above-mentioned light-emitting material. As a result, a specimen to be measured is not limited to a specific material.

4f-4f transition happens easily to the element of the lanthanoid series (hereinafter called as the lanthanoid) when an electron beam is irradiated on the lanthanoid. This makes it possible to measure a stress of a specimen that does not emit light by itself by measuring light emission of the lanthanoid if the lanthanoid is doped on the specimen.

In case of doping the lanthanoid on the specimen, it is preferable that at least one of the elements is selected from the above-mentioned lanthanoid series, especially a family consisting of Sm, Eu, Tb, Yb, La, Er, and Gd. Since the above-mentioned Sm, Eu, Tb, Yb, La, Er, and Gd are high in light emitting efficiency compared with other element of the lanthanoid series, an amount of Sm, Eu, Tb, Yb, La, Er, and Gd to be doped can be lessened. As a result, it is possible to measure a stress of the specimen without changing a property of the specimen.

In case of doping the lanthanoid on the above-mentioned specimen, a ratio of the lanthanoid to the specimen is preferably within a range of 1 ppm~10000 ppm (more preferably within 50 ppm~10000 ppm, furthermore preferably within a range of 100 ppm~10000 ppm). If a ratio of the lanthanoid doped on the specimen is made within the above range, it is possible to detect light emission from the specimen sufficiently. In addition, if the ratio of the lanthanoid doped on the specimen is within the above range, the amount of the lanthanoid included in the specimen is extremely small, thereby not to effect a property of the specimen.

(Stress Measuring Device)

Next, a stress measuring device in accordance with the embodiment will be explained.

The stress measuring device in accordance with the embodiment comprises, as shown in FIG. 1, an electron beam irradiating means 1 (an electron gun 11), a light condensing means 2 (an elliptic mirror 12, an optical fiber 13, an optical fiber controlling unit 14), a spectroscopy means 3 (a monochrometor 15, a monochrometor controlling unit 16, a photo-electron multiplier tube 17), a stress calculating means 4 (a controlling portion 18, a spectrum fitting means 19, a stress map creating means 20), a stage 5, a cooling unit 6, and a temperature controlling unit 7.

Figure 2:
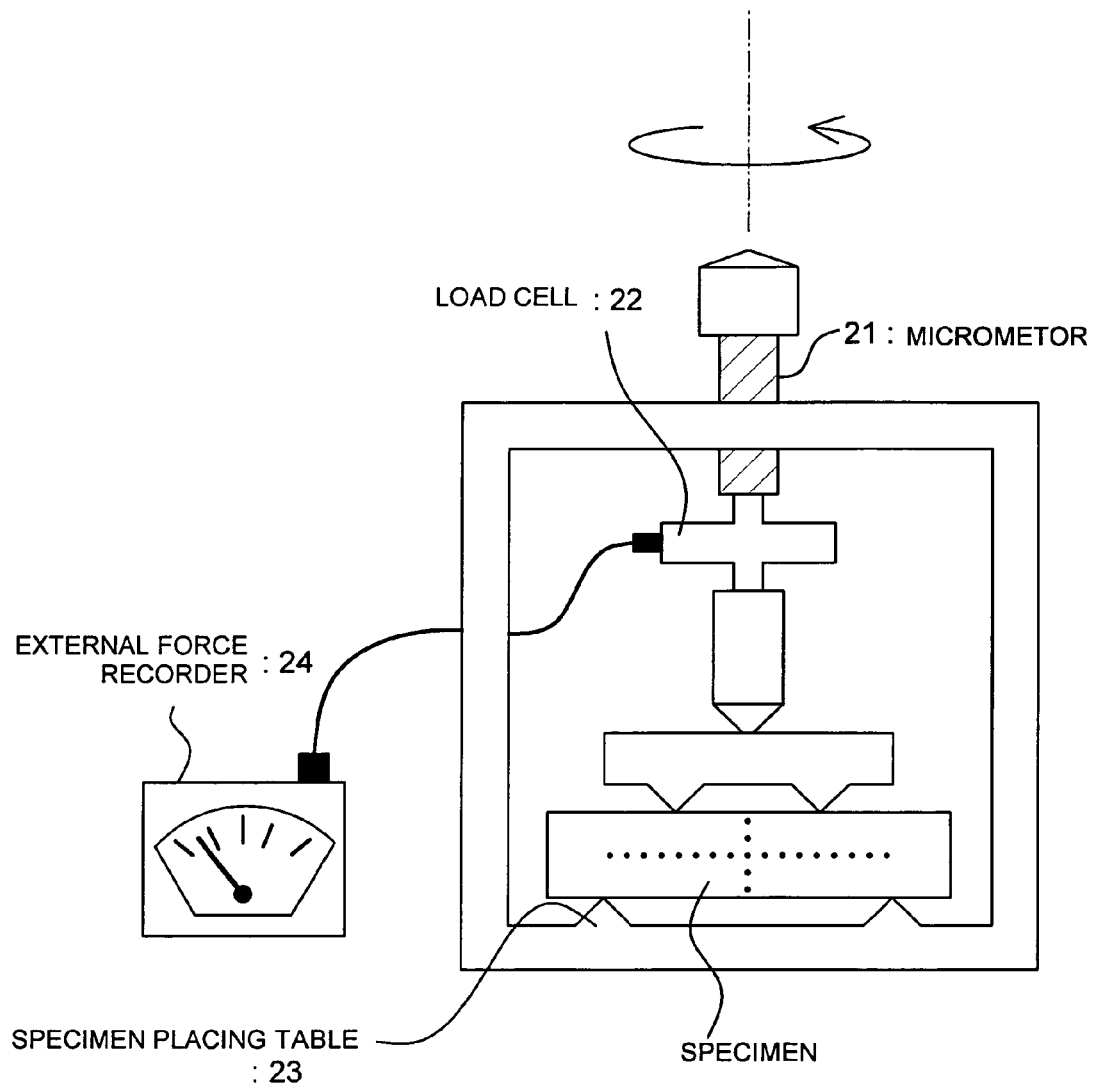
FIG. 2 is a front view showing a general arrangement of an external force impressing unit of the embodiment of the present claimed invention.

In addition, in case of measuring an internal stress, an external force impressing means (not shown in drawings) is arranged. The external force impressing means is to impress an external force on the specimen. More concretely, the external force impressing means is to apply an external force to a surface of the specimen so as to generate an internal stress inside the specimen. The external force impressing means comprises, as shown in FIG. 2, a micrometer 21, a load cell 22, a specimen placing table 23, and an external force recorder 24. A method for impressing an external force on the specimen will be explained. The specimen is placed on the specimen placing table 23, and then the micrometer 21 is rotated so as to impress the external force on the specimen. At this time an amount of the external force impressed on the specimen is converted into an electronic signal. Then the electronic signal is recorded by the external force recorder 24. As mentioned above, a size of the external force impressed on the specimen can be measured.

The above-mentioned electron beam irradiating means 1 is to irradiate an electron beam on a specimen and represented by, for example, the electron gun 11. The electron beam irradiating means 1 includes a condenser lens to make a beam spot diameter of the electron beam small. As a result, the electron beam irradiating means 1 comprises the electron gun 11 and the condenser lens or the like. In addition, an electron microscope, more specifically, a scanning electron microscope may be used as the electron beam irradiating means 1.

The above-mentioned electron gun 11 is to emit an electron beam and so arranged that an electron is emitted from a hot filament or the like. It is preferable that an electron gun of a hot filament electric field open type is used as the electron gun 11.

The light condensing means 2 is to condense light generated by the electron beam irradiated on the specimen. The light condensing means 2 comprises the elliptic mirror 12, the optical fiber 13, and the optical fiber controlling unit 14 or the like. Since the above-mentioned each component is publicly known, an explanation will be omitted.

The elliptic mirror 12 is used to condense light generated by the electron beam irradiated on the specimen. The elliptic mirror 12 is arranged between the electron beam irradiating means 1 and the stage 5 so as not to interrupt irradiation of the electron beam.

The optical fiber 13 and the optical fiber controlling unit 14 are used to introduce the light condensed by the elliptic mirror 12 into the spectroscopy means 3 without a loss.

The spectroscopy means 3 is to detect the light condensed by the light condensing means 2 with a detector and to separate the detected light into monochromatic light with a spectroscope. More concretely, the photo-electron multiplier tube 17 (PMT) can be represented as the above-mentioned detector. In addition, the monochrometor 15 can be represented as the above mentioned spectroscope.

The photo-electron multiplier tube 17 is to amplify the light condensed by the light condensing means 2. Since light emission from the specimen is extremely small, the light emission has to be amplified in order to conduct spectroscopy on the light.

The monochrometor 15 and the monochrometor controlling unit 16 separate the light amplified by the photo-electron multiplier tuber 17 into monochromatic light.

The above-mentioned stress calculating means 4 is to calculate a stress from a spectrum shift between a specimen spectrum and a stress impressed spectrum. More concretely, the stress calculating means 4 is to calculate a residual stress from a spectrum shift between a stress impressed spectrum wherein a residual stress exists in the specimen and a specimen spectrum wherein no residual stress exists in the specimen. In addition the stress calculating means 4 is also to calculate an internal stress from a spectrum shift between a stress impressed spectrum wherein an internal stress exists in the specimen and a specimen spectrum wherein no internal stress exists in the specimen. The stress calculating means 4 standardizes, more specifically, for example, a stress impressed spectrum (an internal stress impressed spectrum) wherein a residual stress (or an internal stress) exists in the specimen and a specimen spectrum wherein no residual stress (or an internal stress) exists in the specimen respectively by making use of a predetermined function. The stress calculating means 4 also includes a program that calculates a stress by calculating a spectrum shift based on the standardized spectrum.

In addition, the stress calculating means 4 can also obtain a correlation between the spectrum shift and a predetermined external force. The spectrum shift differs depending on kinds of the specimen. In other words, if a specimen to be measured differs, a correlation between an external force applied to the specimen and a peak shift due to the external force varies. As a result, in case that a correlation between an external force applied to the specimen and a peak shift due to the external force is unknown, a correlation between a size of an external force and a spectrum shift has to be obtained. In order to obtain the above-mentioned correlation by the stress calculating means 4, constant external force is applied to the specimen by the external force impressing means and a spectrum shift obtained at this time is recorded. Then a correlation between a size of an external force and a spectrum shift is obtained by repetition of the above operation with varying a size of the external force.

The stage 5 is used to place a specimen. The stage 5 keeps a temperature of the specimen at a constant by making use of the temperature controlling unit 7. More concretely, for example, in case that temperature of the specimen goes up, the stage 5 is cooled down because cooling agency such as liquid nitrogen, liquid helium or the like is supplied with the stage 5. As a result, the specimen is cooled down. For example, there is an atomic arrangement or a molecular structure that may vary depending on temperature for specimen of, for example, organic matter such as biomacromolecule or the like. In case of using the above-mentioned specimen, there is a possibility that an accurate stress can not be measured if temperature of the specimen varies due to an electron beam irradiated on the specimen. As a result, it is possible to measure the stress more accurately if the temperature of the specimen is kept constant.

In addition, in case that a stress of the specimen is measured along a direction of a surface of the specimen, the stage 5 may be an automatic variable x-y stage. In other words, the stress of the specimen may be two-dimensionally measured (stress mapping) by moving the stage 5 along the direction of the surface of the specimen. Furthermore, the stress mapping may be conducted by changing an irradiated angle of an electron beam irradiated by the electron beam irradiating means 1. The stress mapping will be described later.

It is preferable that the stress measuring device in accordance with this embodiment further comprises an external light irradiating means that irradiates an external light whose spectrum is known.

The above-mentioned external light irradiating means is to emit light having a predetermined wave length, more specifically, a halogen light (a neon light) or the like. Since the halogen light emits light having a predetermined wave length, the obtained spectrum includes a peak as being a reference when spectroscopy is conducted on light from the halogen light in conjunction with the light emission obtained by irradiating an electron beam on a specimen in measuring the stress. It is possible to measure a stress accurately at any time by conducting compensation on each spectrum (the specimen spectrum, the stress impressed spectrum and the internal stress impressed spectrum) based on the peak of the spectrum as being the reference.

More concretely, in obtaining each spectrum, spectroscopy is also conducted on an external light in conjunction with the light emission from the specimen. On an occasion of calculating a spectrum shift between, for example, a specimen spectrum and a stress impressed spectrum, if a position of a spectrum of the external light included in the specimen spectrum is made to coincide with a position of a spectrum of the external light included in the stress impressed spectrum, an error can be minimized resulting from a measurement environment, thereby calculating the spectrum shift more accurately. In addition, spectra measured by different measuring devices can also be compared.

(Stress Measuring Method)

The stress measuring method in accordance with this embodiment includes an electron beam irradiating process wherein an electron beam is irradiated on a specimen, a light concentrating process wherein light emission from the specimen in the electron beam irradiating process is concentrated, a spectroscopy process wherein spectroscopy is conducted on light concentrated in the light concentrating process so as to obtain a spectrum, and a stress calculating process wherein a stress is obtained from a spectrum shift between a specimen spectrum wherein no stress exists in the specimen and a stress impressed spectrum wherein a stress exists in the specimen.

It is preferable that the stress measuring method in accordance with this embodiment further comprises an external force impressing process wherein external force is applied to the specimen prior to the above-mentioned electron beam irradiating process and a stress is obtained in the stress calculating process based on a spectrum shift between an internal stress impressed spectrum wherein an internal stress is generated in the specimen by the external force impressing process and the above-mentioned specimen spectrum or the above-mentioned stress impressed spectrum.

Figure 3:
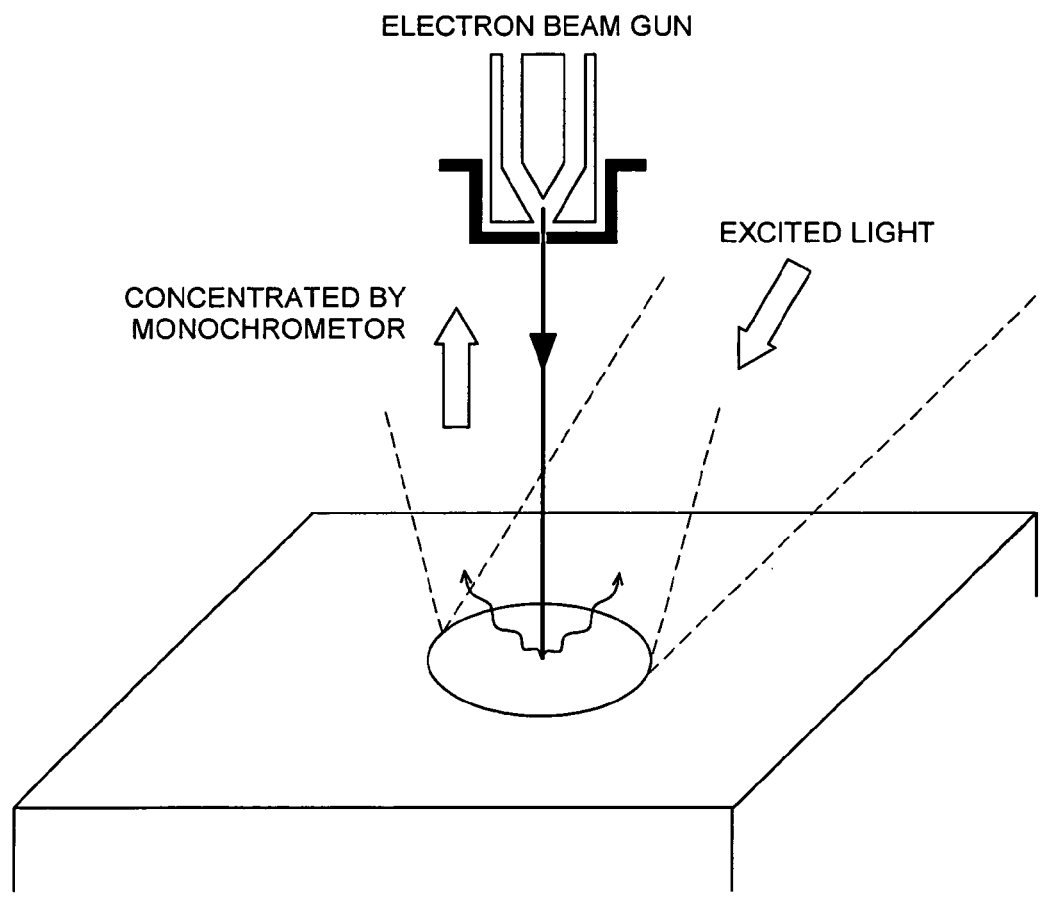
FIG. 3 is a perspective view showing a difference of a size of a beam spot diameter between an electron gun in accordance with the embodiment of the present claimed invention and a conventional laser light.
Figure 4:
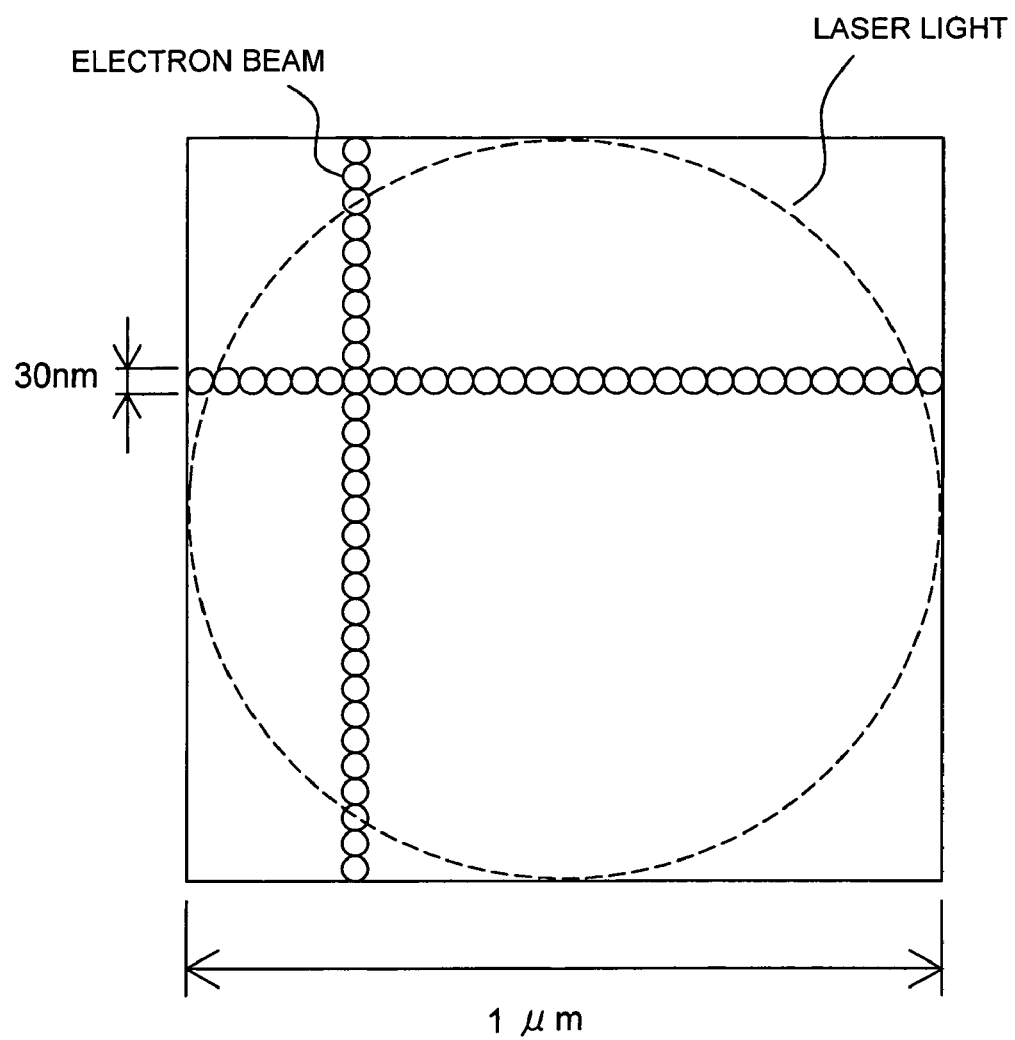
FIG. 4 a plane view showing a difference of a size of a beam spot diameter between an electron gun in accordance with the embodiment of the present claimed invention and a conventional laser light.

In the electron beam irradiating process an electron beam is irradiated on the specimen. And light emission is obtained from the specimen by irradiating the electron beam on the specimen. More concretely, if an electron beam having a specific wavelength is irradiated on the specimen, an electronic state of a specific electron of the specimen is excited and light is emitted at a time when the excited state is returned to a normal state. A diameter of a beam spot of the electron beam that is irradiated on the specimen may be varied according to a place where a stress is measured and a kind of the specimen or the like. In this invention, the diameter of the beam spot can be narrowed down to not greater than 100 nm, more preferably not greater than 10 nm, furthermore preferably not greater than 1.5 nm, and the most preferably about 0.13 nm. If the diameter of the beam spot is narrowed down to not greater than 100 nm, the diameter of the beam spot can be made significantly small as shown in FIG. 3 and FIG. 4 compared with a conventional arrangement of irradiating laser light on a specimen. More concretely, in accordance with a conventional arrangement of irradiating laser light on a specimen, a diameter of a beam spot is about 1 μm, about 200 nm for a case of proximity field light, however, in accordance with this invention the diameter of the beam spot can be made not greater than 100 nm (30 nm in FIG. 4) as mentioned above.

In the light concentrating process, the light generated in the electron beam irradiating process is concentrated by the elliptic mirror 12. The concentrated light is transmitted to the monochrometor 15 and the photo-electron multiplier tube 17 through the optical fiber 13.

In the spectral process, the light transmitted to the photo-electron multiplier tube 17 is amplified and then transmitted to the monochrometor 15. Next, the monochrometor 15 conducts spectroscopy on the amplified light so as to obtain a spectrum. Then frequency of the light directly transmitted to the monochrometor 15 is measured accurately and a peak shift can be determined.

Next, the stress calculating process will be explained. In the stress calculating process, in case of measuring a residual stress, a stress is calculated based on a spectrum shift between a specimen spectrum wherein no stress exists in the specimen and a stress impressed spectrum wherein a residual stress exists in the specimen. In addition, in case of measuring an internal stress generated in the specimen, a stress is measured based on a spectrum shift between the internal stress impressed spectrum and the stress impressed spectrum or the specimen spectrum.

In addition, in case that a correlation between an amount of an external force impressed on the specimen and an amount of the above-mentioned spectrum shift is unknown, a correlation calculating process has to be conducted prior to the stress calculating process. In the correlation calculating process, a correlation between the amount of the external force impressed on the specimen and the amount of the above-mentioned spectrum shift is obtained. In order to obtain the above-mentioned correlation, a constant external force is applied to the specimen by the external force impressing means and the spectrum shift obtained at this time is recorded. Then a correlation between a size of the external force and the spectrum shift is obtained by repetition of the above operation with varying a size of the external force.

Next, a correlation between a size of an external force and a spectrum shift will be explained. A relationship between a stress generated in the specimen due to an external force and a spectrum shift (more concretely, an amount of a peak shift of a spectrum) can be linearly approached to an extent of several GPa of a size of an external force. More concretely, a correlation between a size of an external force and a spectrum shift is shown by the following expression (1).
(Expression 1)

$$v_\sigma = v_0 + (\partial v / \partial \sigma) \partial \sigma \quad (1)$$

where, $v_0$ corresponds to a center wave number of a peak of a spectrum in a state that a stress is zero, $v_\sigma$ a is a center wave number of a peak of a spectrum at a time the external force is σ, σ is a size of a stress generated by the external force. Inside the parenthesis is generally called as a PS (Piezo-Spectroscopic) coefficient and expressed as Π, and is a tensor that depends on a stress alone and does not depend on a position. As a result, a shift amount due to an external force of a peak of a spectrum $\Delta v = v_\sigma - v_0$ is a relationship shown by the following expression (2).
(Expression 2)

$$\Delta v = \Pi_{ij} \cdot \sigma_{ij} (i,j=1,2,3) \quad (2)$$

It must be noted that each of the above-mentioned $\Pi_{ij}$ and $\sigma_{ij}$ is a tensor.

As a result, it must be noted that a value of Π varies depending on a case that a stress due to an external force is applied to one axis, a case that a stress due to an external force is applied to two axes, and a case that a stress due to an external force is applied to three axes. In addition, it must be noted that there is a specimen whose $\Pi_{ij}*(i=1, 2, 3)$ for each axis can be considered equal such as an isotropy specimen, however, the specimen having anisotropy such as alumina ($Al_2O_3$) doped with chromes (Cr) is not always equal and may be different.

It is very important to specify a spectrum accurately in a state that a stress is zero for a purpose of certifying a high space resolution and a measurement of a very little stress change. In the above-mentioned electron beam irradiating process of this embodiment, an electron beam is irradiated without narrowing down to one or multiple broad areas AR that are sufficiently bigger than a spot size of an electron beam to obtain a required space resolution.

Figure 5:
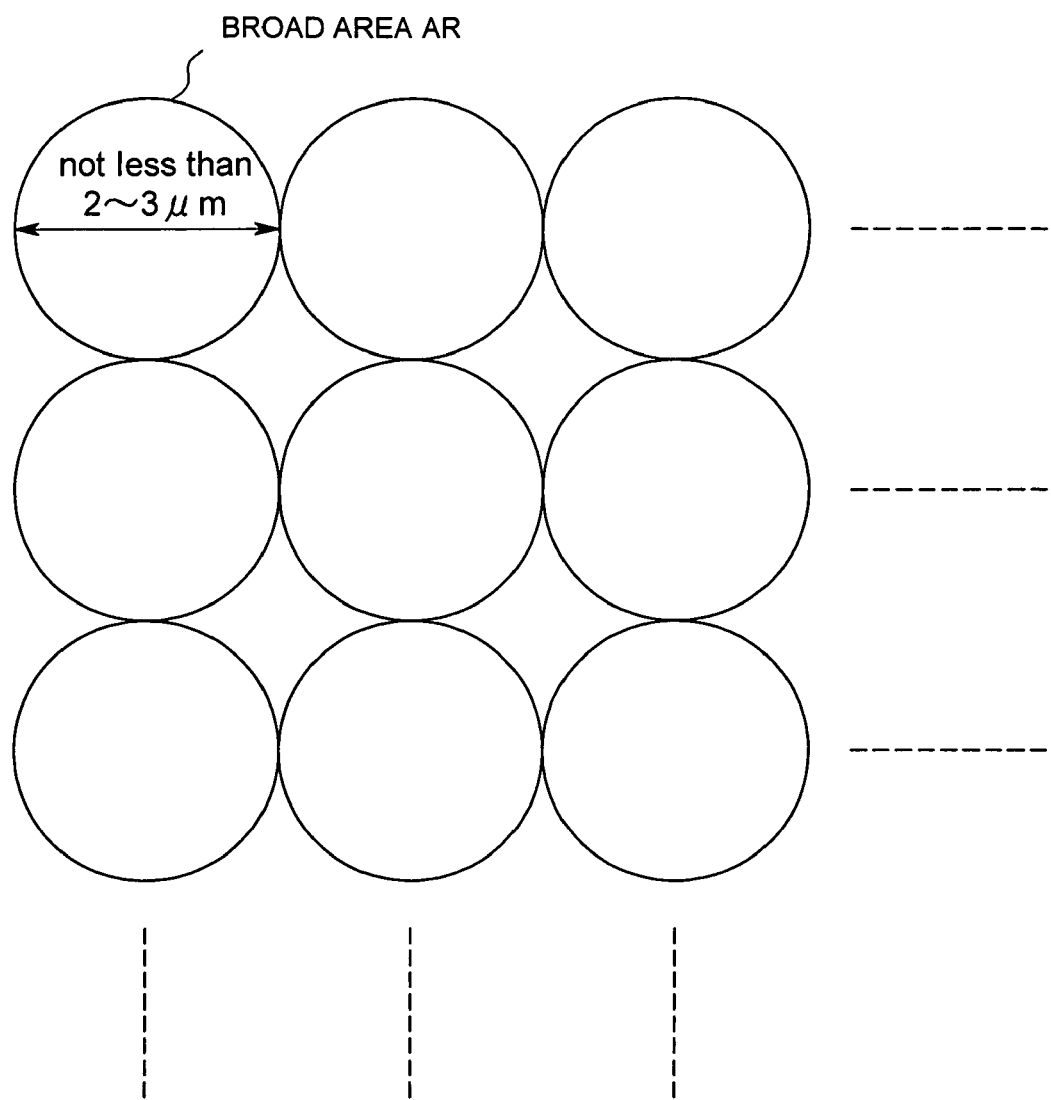
FIG. 5 is a plane view showing a mode wherein an electron beam is irradiated without narrowing down on the specimen in case of obtaining a spectrum of a specimen in accordance with the embodiment of the present claimed invention.
Figure 6:
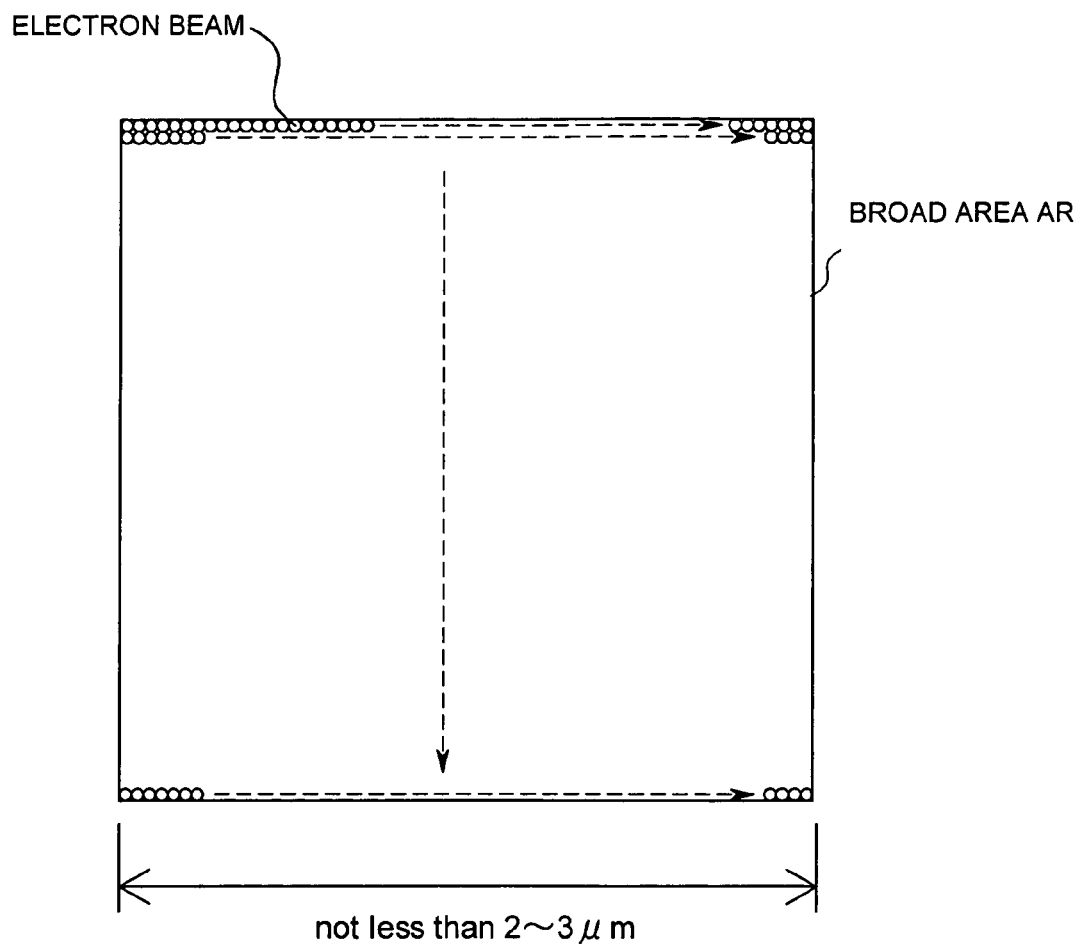
FIG. 6 is a plane view showing a mode wherein an electron beam is irradiated on the specimen by scanning in case of obtaining a spectrum of a specimen in accordance with the embodiment of the present claimed invention.

More concretely, as shown in FIG. 5, electron beams are irradiated without narrowing down on multiple broad areas AR whose size is set bigger in over two figures (not less than 100 times, not less than 2~3 μm in this embodiment) of a spot size of an electron beam to obtain a required space resolution in a state that no external force is applied to the specimen and then a mean value of the spectra of the light obtained in each broad area AR is set as the above-mentioned specimen spectrum. If the area is big enough, the stress existing in the area AR can be estimated zero in total, in spite of a margin of plus or minus of the local stress, which makes it possible to consider a mean value of the spectra of the light obtained in each broad area AR as a spectrum in condition of a residual stress zero, in other words, a specimen spectrum.

It is a matter of course that an electron beam may be scanned and irradiated with a spot size to obtain a required space resolution or a spot size a little bigger than the spot size to obtain the required space resolution on one or multiple broad areas AR and then a mean value of the light spectra obtained by irradiation of each electron beam may be considered as a specimen spectrum. In this embodiment, the electron beam is scanned along a crosswise direction and then shifted along a longitudinal direction sequentially so as to scan the electron beam over the broad area AR.

If the electron beam is irradiated on all over the area of the specimen so as to obtain a mean light spectrum, the specimen spectrum can be specified more accurately. In addition, the above-mentioned method to specify the specimen spectrum can be applied to not only a measurement of a stress by irradiation of an electron beam but also a measurement of a stress by irradiation of light (including general electromagnetic waves).

Furthermore, in case that the specimen is of, for example, a semiconductor material, composition of the specimen may differ locally due to proliferation of doped impurities. In this case, a chemical shift is generated in the spectrum due to a difference of composition, which should be taken into consideration, otherwise an error might be mixed into the specimen spectrum.

In order to prevent this, in this embodiment a composition analysis process that analyses a local composition difference of the specimen is further conducted and in the above-mentioned stress calculating process the specimen spectrum is determined in consideration of the spectrum shift generated from a difference of components of the spectrum for each area whose specimen component differs and that is obtained in the above-mentioned component analysis process. In the component analysis process a well-known nondestructive analysis method may be used.

As another method to obtain the specimen spectrum, a minute amount sample obtaining process that obtains a minute amount of a sample from the specimen is conducted and then the light spectrum obtained by irradiating an electron beam on a minute amount of the sample may be considered as the above-mentioned specimen spectrum. In order to obtain the minute amount of the sample, for the sake of measurement it is preferable that, for example, a nano-manipulator is used and the measurement is conducted under the same environment as that of the electron beam irradiation, namely, in a vacuum.

As a method for measuring a residual stress of a specimen by the use of the stress measuring method in accordance with the embodiment, for example, a following method may be used.

First, measure a peak shift in case that predetermined external force is applied to a specimen having no residual stress and obtain a correlation between the external force applied to the specimen and the peak shift (first process).

Next, generate a residual stress in the specimen by applying an extremely big pressure (for example, Vickers indentation) and/or heat locally. More concretely, for example, in case that the specimen whose stress is to be measured is glass, it is possible to obtain a specimen in a state that a residual stress exists by applying heat to the specimen to be melted followed by rapid cooling. Then measure a spectrum in a state that the above-mentioned residual stress exists, namely, a stress impressed spectrum (second process).

Next, measure a spectrum of the specimen in a state that no residual stress exists, namely, a specimen spectrum (third process). The specimen in the state that "no residual stress exists" is the specimen in a state that no residual stress exists inside the specimen. As a method to realize the state that "no residual stress exists inside the specimen", in this embodiment, for example, a mean value of the light spectra obtained in the broad area is used because of a merit that the measurement can be conducted nondestructively, however, a method for crushing the specimen into fine particle or a method for provide a annealing process may be used.

In addition, calculate a peak shift of the above-mentioned stress impressed spectrum and a peak shift of the specimen spectrum (fourth process).

At this time, a difference among the maximum values of the peaks may be obtained or a difference among half value widths of peaks may be obtained as a method for calculating the spectrum shift.

Apply the obtained peak shift value into the above-mentioned correlation (fifth process), which makes it possible to measure a residual stress remaining in the specimen.

In case that the correlation (a relationship) between the external force applied to the specimen and the peak shift is known, the first process may be omitted.

In addition, for example, a residual stress accumulated in the specimen may be measured by a process of measuring a stress at a time when a product is manufactured and then measuring a stress of the above-mentioned product again after using the product for a certain period.

In case that the specimen whose stress is to be measured does not emit light by itself, namely, the specimen does not emit light even though an electron beam is irradiated on the specimen, a doping process to dope the specimen with the lanthanoid may be conducted prior to the first process.

In case of measuring an internal stress of a specimen, instead of the above-mentioned third process, an internal stress impressed spectrum in a state that an external stress is applied to the specimen is measured (apostrophe third process) by the use of the external force impressing means. In the fifth process, an internal stress is measured from the spectrum shift between the internal stress impressed spectrum and the stress impressed spectrum. In addition, the above-mentioned apostrophe third process and the second process may be conducted before and behind. Namely, the second process may be conducted after the apostrophe third process.

In addition, it is possible to measure both the internal stress and the residual stress of the specimen by conducting all of the above-mentioned second process, the third process and the apostrophe third process. More concretely, the residual stress can be obtained from the spectrum shift between the stress impressed spectrum obtained in the second process and the specimen spectrum obtained in the third process. And the internal stress can be obtained from the spectrum shift between the stress impressed spectrum obtained in the second process and the internal stress impressed spectrum obtained in the apostrophe third process.

In case of measuring both the internal stress and the residual stress by conducting the above-mentioned second process, the third process and the apostrophe third process, the second process and the apostrophe third process may be conducted before and behind as far as the residual stress of the specimen does not change in the second process and the apostrophe third process. The residual stress of the specimen might vary when the specimen is changed from a state that an external force is applied to a state that no external force is applied. For example, if rearrangement of molecule of the specimen happens, the residual stress varies. If the residual stress of the specimen changes due to the external force impressing means, it is not possible to measure the residual stress accurately. As a result, it is preferable that the apostrophe third process is conducted after the second process. In addition, it is more preferable that the third process is conducted after the second process and the apostrophe third process. The reason is, for example, if the specimen is crushed into fine particles in the third process, it is not possible to conduct the second process and the apostrophe third process.

As a result, it is more preferable to conduct the second process, the apostrophe third process and the third process in sequence in order to measure both the internal stress and the residual stress.

The above-mentioned specimen spectrum, the stress impressed spectrum and the internal stress impressed spectrum may be measured at the same portion of the specimen, or may be measured at different portions of the specimen. For example, in order to obtain the internal stress impressed spectrum and the specimen spectrum at the same portion of the specimen, first the specimen is fixed and then the specimen spectrum is measured. And then the internal stress impressed spectrum in a state that the external force is impressed on the specimen is measured.

Next, how the spectrum shift is obtained will be explained.

Figure 7:
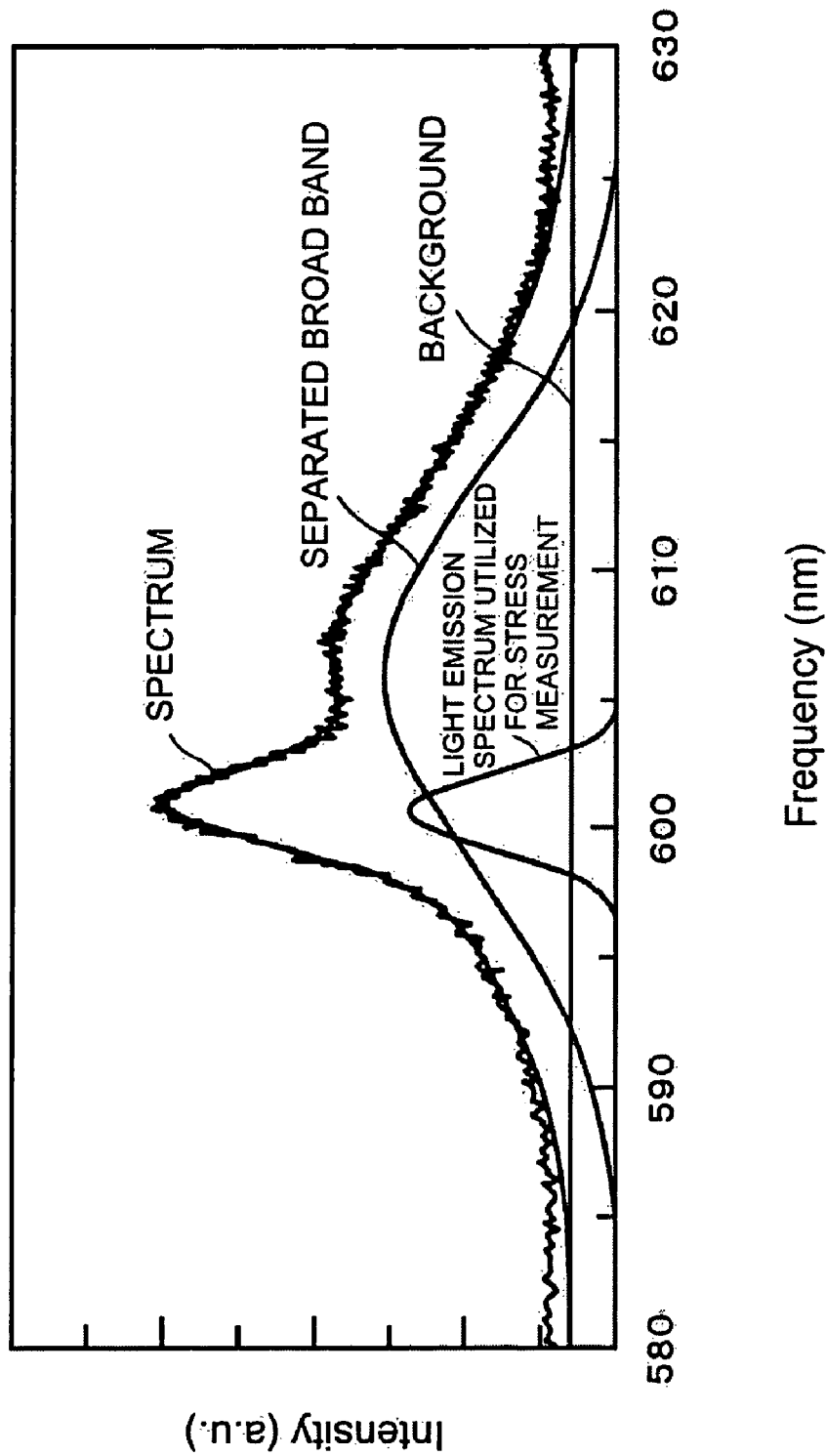
FIG. 7 is a graph showing a spectrum obtained by irradiating an electron beam on the specimen in accordance with the embodiment of the present claimed invention.

First, an electron beam whose wave length is continuous is irradiated on the specimen so as to obtain a spectrum. This makes it possible to obtain a peak (wave form) peculiar to the specimen. Then a spectrum of light obtained by irradiating the above-mentioned wavelength can be obtained. The spectrum includes, as shown in FIG. 7, noise or a background at a time of measurement. As a result, in order to remove the noise or the background, the obtained spectrum is spectroscopic-compensated and standardized by a specific function. Then a light emission spectrum (the specimen spectrum) of the specimen can be obtained by removing the background. Then obtain a portion where the peak is big. The same applies to a state that an external force is applied to the specimen and a spectrum is obtained by irradiating the above-mentioned electron beam on the specimen in a state that an external force is applied. Then a light emission spectrum (the internal stress impressed spectrum) of the specimen in a state that an external force is applied can be obtained by providing the same process as the above.

As mentioned above, in order to obtain the spectrum shift between the measured specimen spectrum and the stress impressed spectrum, peak shifts of the peaks whose shift amount of both spectra is the maximum may be measured. In addition, as a method for measuring a spectrum shift, the shift amount may be measured by making use of half value width of the peaks of both spectra. The internal stress may be measured with the same method.

The stress measuring method in accordance with the present claimed invention enables structural analysis or a stress measurement at a level of atom or molecule. More concretely, for example, a stress measurement of amorphous ceramics, an analysis of semiconductor process, a stress analysis of a micro machine such as a spring or an actuator or a stress analysis of a carbon nanotube/nano-coil can be conducted. In addition, a stress measurement of bones may also be conducted.

Next, a stress mapping will be explained.

In order to conduct a method for measuring a stress applied to the specimen along a surface of the specimen and displaying the measured stress, namely, to conduct a two-dimensional mapping, for example, an electron beam is irradiated on the specimen with moving the stage 5 so as to measure the stress along the surface of the specimen. In addition, as another method, for example, an electron beam is pulsed by the use of a pulse generator and a beam blanking unit.

The pulse generator and the beam blanking unit are used to pulse the electron beam irradiated from the electron beam irradiating means 1. The pulsed electron beam is irradiating on the specimen with changing an irradiating angle, which makes it possible to irradiate the electron beam on the specimen along the surface of the specimen without moving the stage 5.

The stress mapping can be conducted by measuring the stress toward a direction of the surface of the specimen.

As mentioned above, the stress measuring method in accordance with this embodiment includes the correlation calculating process that calculates a correlation between the amount of the external stress impressed on the specimen and the amount of the spectrum shift, the electron beam irradiating process that irradiates the electron beam on the specimen, the spectral process that obtains the spectrum by separating light generated from the specimen by the above-mentioned electron beam irradiating process, and the stress calculating process that obtains the stress from the spectrum shift between the specimen spectrum in a state that no stress exists in the specimen and the stress impressed spectrum in a state that a stress exists in the specimen.

In accordance with the above-mentioned arrangement, the stress is measured by the use of the light generated by irradiating the electron beam on the specimen. More concretely, a residual stress is calculated from a difference between the specimen spectrum obtained by irradiating the electron beam on the specimen and the internal stress impressed spectrum obtained by irradiating the electron beam on the specimen on which the external force is impressed by the above-mentioned external force impressing process.

In addition, the internal stress can be measured if an external force impressing process that applies the external force to the specimen is included prior to the above-mentioned electron beam irradiating process and the above-mentioned stress calculating means obtains a stress from the spectrum shift between the internal stress impressed spectrum in a state that an internal stress is generated in the specimen by the external stress impressing process and the above-mentioned specimen spectrum or the above-mentioned stress impressed spectrum.

Since the above-mentioned electron beam is short in wavelength compared with laser light conventionally used for measuring a stress, it is possible to make a beam spot small. As a result, an arrangement (electroluminescence spectroscopy) for measuring a stress by the use of light generated by irradiating an electron beam on a specimen can measure a stress that is superior in a positional resolution (a space resolution) compared with a conventional arrangement (photoluminescence spectroscopy) for measuring a stress by the use of light generated by irradiating conventional light. More concretely, in case of using an electron beam, since it is possible to make a diameter of a beam spot small not more than 100 nm, more preferably not more than 10 nm, furthermore preferably not more than 2 nm, the most preferably to an extent of 0.13 nm, it is possible to measure a stress whose positional resolution is extremely high compared with the conventional arrangement.

Since this makes it possible to measure a stress in a high positional resolution (in several nm unit), a stress can be analyzed in a level of atom/molecule regarding to a microscopic portion such as a carbon nanotube or a micro machine whose stress has not been measured by the conventional stress measuring method wherein a diameter of a beam spot is big. A structure of the specimen can also be estimated based on a calculated stress.

In addition, the arrangement for measuring a stress by making use of light emission obtained by irradiating an electron beam on a specimen can make a spectrum shift big as proven by an experiment compared with a conventional arrangement of irradiating laser light. As a result, the spectrum shift can be measured more accurately, thereby to measure a stress with a high resolution. Furthermore, in case of a specimen whose stress can not be measured because the spectrum shift is small by the conventional arrangement, it becomes possible to measure a spectrum shift by using an electron beam for measurement.

In addition, if a correlation calculating process that calculates a correlation between an amount of an external force impressed on a specimen and an amount of the above-mentioned spectrum shift is conducted prior to the stress calculating process, a stress (an internal stress, a residual stress) applied to the specimen can be calculated even though a correlation between the amount of the external force impressed on the specimen and the amount of the above-mentioned spectrum shift is unknown.

It is more preferable that external light whose spectrum frequency is known is irradiated in the above-mentioned electron beam irradiating process, spectroscopy is conducted on the external light in conjunction with the light emission from the specimen so as to obtain a spectrum in the spectroscopy process, and each spectrum position of the above-mentioned specimen spectrum and the stress impressed spectrum is compensated in the above-mentioned stress calculating process. Like the same, an internal stress can be compensated by the use of the external force.

Figure 8:
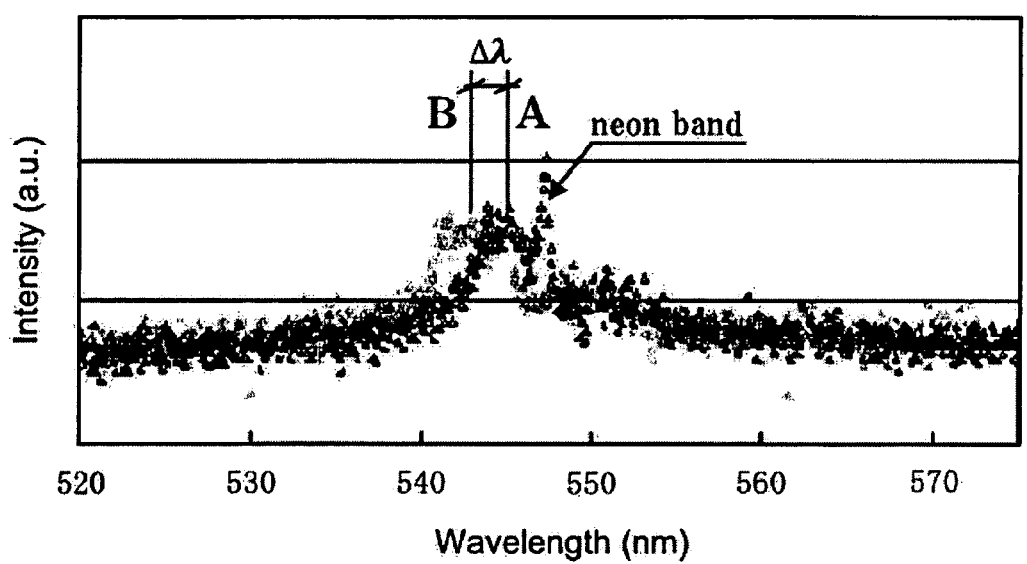
FIG. 8 is a graph showing a spectrum of external light in accordance with the embodiment of the present claimed invention.

The external light is light that is irrelevant to light emission from a specimen and whose spectrum is known. In this example, as shown in FIG. 8, a predetermined peak wavelength as being a reference for the above-mentioned external spectrum is set near each predetermined peak wavelength of a specimen spectrum to be compared and a stress impressed spectrum, more concretely, about within an amount twice as much as a half value width of the predetermined peak wavelength of the specimen spectrum and the stress impressed spectrum. Each spectrum position of the specimen spectrum and the stress impressed spectrum is compensated based on a spectrum of the external light. More concretely, spectroscopy is conducted on each spectrum together with the external light in obtaining each spectrum, and spectra of the external light included in both of the specimen spectrum and the stress impressed spectrum are made to coincide each other in calculating a spectrum shift between the specimen spectrum and the stress impressed spectrum.

This makes it possible to minimize an error originating in a measuring environment, thereby to calculate the spectrum shift more accurately. In addition, spectra that are measured by different measuring devices can also be compared. Especially in case of the stress measuring device that is superior in a positional resolution and sensitivity, an arrangement wherein a fitting error can be automatically compensated is especially preferable because a slight environmental variation is directly linked to an error.

Since the above-mentioned specimen is made by doping at least one element selected from a family consisting of the lanthanoid by an amount within a range of 1 ppm~10000 ppm, it is possible to measure a stress even though the specimen does not emit light when an electron beam is irradiated. As a result, in accordance with the above-mentioned arrangement, it is possible to measure light generated due to 4f-4f transition of the lanthanoid when the specimen is doped with an element of the lanthanoid by an amount within a range of 1 ppm~10000 ppm, which makes it possible to measure the stress.

In addition, since an element of the lanthanoid can obtain a clear spectra despite of a little amount, a ratio of the element to the specimen is preferably an extremely small amount (within a range of 1 ppm~10000 ppm), more preferably within 50 ppm~10000 ppm, and furthermore preferably within a range of 100 ppm~10000 ppm. This makes it possible to measure the stress without changing a property (physicality) of the specimen.

Furthermore, it is preferable that the above-mentioned lanthanoid is at least one element selected from a family consisting of Sm, Eu, Tb, Yb, La, Er, and Gd.

The stress measuring method in accordance with this embodiment may have an arrangement including a first step to obtain a specimen spectrum by separating light emission obtained by irradiating an electron beam on a specimen in which no internal stress exists, a second step to obtain an internal stress impressed spectrum by separating light emission obtained by irradiating an electron beam on the specimen in which an internal stress exists by applying an external force to the specimen, and a stress calculating step to obtain a stress from a difference between the specimen spectrum obtained in the above-mentioned first step and the internal stress impressed spectrum obtained in the above-mentioned second step.

In addition, the stress measuring method in accordance with this embodiment may have an arrangement including a first step to obtain a specimen spectrum by separating light emission obtained by irradiating an electron beam on a specimen in which no residual stress exists, a second step to obtain a residual stress impressed spectrum by separating light emission obtained by irradiating an electron beam on the specimen in which a residual stress exists, and a stress calculating step to obtain a stress from a difference between the specimen spectrum obtained in the above-mentioned first step and the residual stress impressed spectrum obtained in the above-mentioned second step.

In addition, the stress measuring method in accordance with this embodiment may have an arrangement including an external force impressing process to apply an external force to a specimen, an electron beam irradiating process to irradiate an electron beam on the specimen, a spectroscopy process to obtain a spectrum by separating light emission generated from the specimen in the electron beam irradiating process, and a stress calculating process to obtain a stress from a spectrum shift between a specimen spectrum obtained by irradiating the electron beam on the specimen and a stress impressed spectrum obtained by irradiating the electron beam on the specimen in a state that a stress exists due to the above-mentioned external force impressed process.

Furthermore, the stress measuring method in accordance with this embodiment may have an arrangement including an external force impressing process to apply an external force to a specimen, a spectroscopy process to obtain a spectrum by separating light obtained due to cathode luminescence, and a stress calculating process to obtain a stress from a difference between an internal stress impressed spectrum of the specimen to which the external force is applied in the above-mentioned external force impressing process and a specimen spectrum obtained by irradiating an electron beam on the specimen in a state that no internal stress exists.

The cathode luminescence is a phenomenon wherein electromagnetic waves (light) having wavelengths of ultraviolet, visible and infrared regions are emitted from the specimen by irradiating an electron probe (an electron beam) on the specimen.

In accordance with the above-mentioned arrangement, since spectroscopy is conducted by the use of the cathode luminescence in the spectroscopy process, it is possible to conduct a stress measurement with a higher positional resolution and a higher stress resolution compared with a conventional spectroscopy process by the use of photoluminescence.

{Embodiment}

(Creation of a Specimen to be Measured)

Glass as being a specimen to measure a stress was made by mixing SmF3 powder into borosilicate glass so that a final concentration came to 10000 ppm, followed by a general melting rapid cooling method.

(Stress Measuring Method)

A scanning electron microscope (manufactured by JEOL, Ltd., Type; JSM-6500F) comprising an electron beam gun 11 of a hot filament electric field emission type with a resolution of 1.5 mm was used as the electron irradiating means 1. The above-mentioned scanning electron microscope was placed inside a cutout on an air suspension type optical table in order to adjust an optical system and to prevent vibration. In addition, a high sensitive cathode luminescence detecting unit (manufactured by Atago Bussann Co. Ltd., Type; MP-32FE) having a triple monochrometor 15 comprising an elliptical mirror, an optical fiber 13, and a CCD camera was used as the light condensing means 2 and the spectroscopy means 3. A mapping unit and its related software (manufactured by Atago Bussann Co. Ltd., Type; PMT R943-02) were used as the stress calculating means 4.

[Embodiment 1]

First, a correlation of a specimen between a peak shift and the external force was obtained. More concretely, an electron was poured into the specimen so that a diameter of a beam spot became 30 nm with the minimum diffusion toward a lateral direction in a state that no external force was impressed on the specimen with an accelerating voltage set at 1.5 kV and then spectroscopy was conducted on light emission from the specimen by a spectroscope so as to obtain a spectrum. As a result, approximately 1000 spots existed in 1 µm square. And then a mean value of spectra obtained from the beam spot irradiated on an area of the above-mentioned 1 µm square was obtained. A measuring range of the diameter of the beam spot can be narrowed down by setting a magnifying power.

Figure 9:
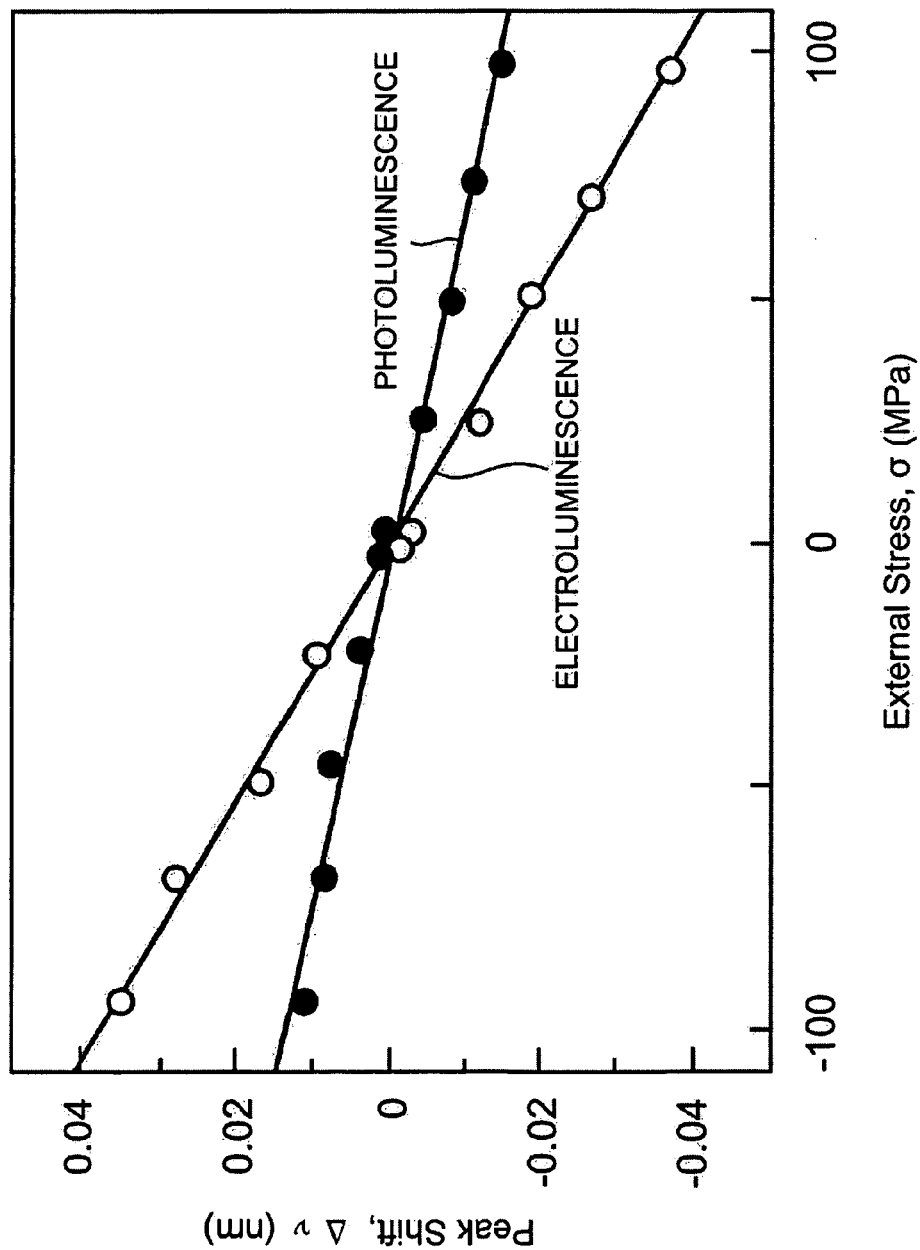
FIG. 9 is a graph showing a contrast between a correlation of a peak shift to an amount of an impressed external force for an embodiment 1 and a comparative example and a peak shift to an amount of an impressed external force in case of using conventional laser light.

Next, a spectrum was obtained with impressing a predetermined external force on the specimen. Then a peak shift was measured by impressing the predetermined external force on the specimen. More concretely, the strongest peak in strength or a peak whose shape was clear was selected among spectra in a state that no external force was impressed. Then a spectrum shift between a spectrum of the selected peak in a state that no external force was impressed and a spectrum in a state that an external force was impressed was calculated. A correlation between the spectrum shift and the external force was obtained as shown in FIG. 9 by conducting the above-mentioned process with changing a magnitude of the external force. The obtained spectrum was standardized by the use of a predetermined function and a difference between the maximum values of the peaks of both spectra was considered to be the peak shift.

"Photoluminescence" (●) shows a correlation between a peak shift and an amount of an external force in case that conventional laser light is used, and "electroluminescence" (○) shows a correlation between a peak shift and an amount of an external force in case that an electron beam in accordance with this invention is used.

Figure 10:
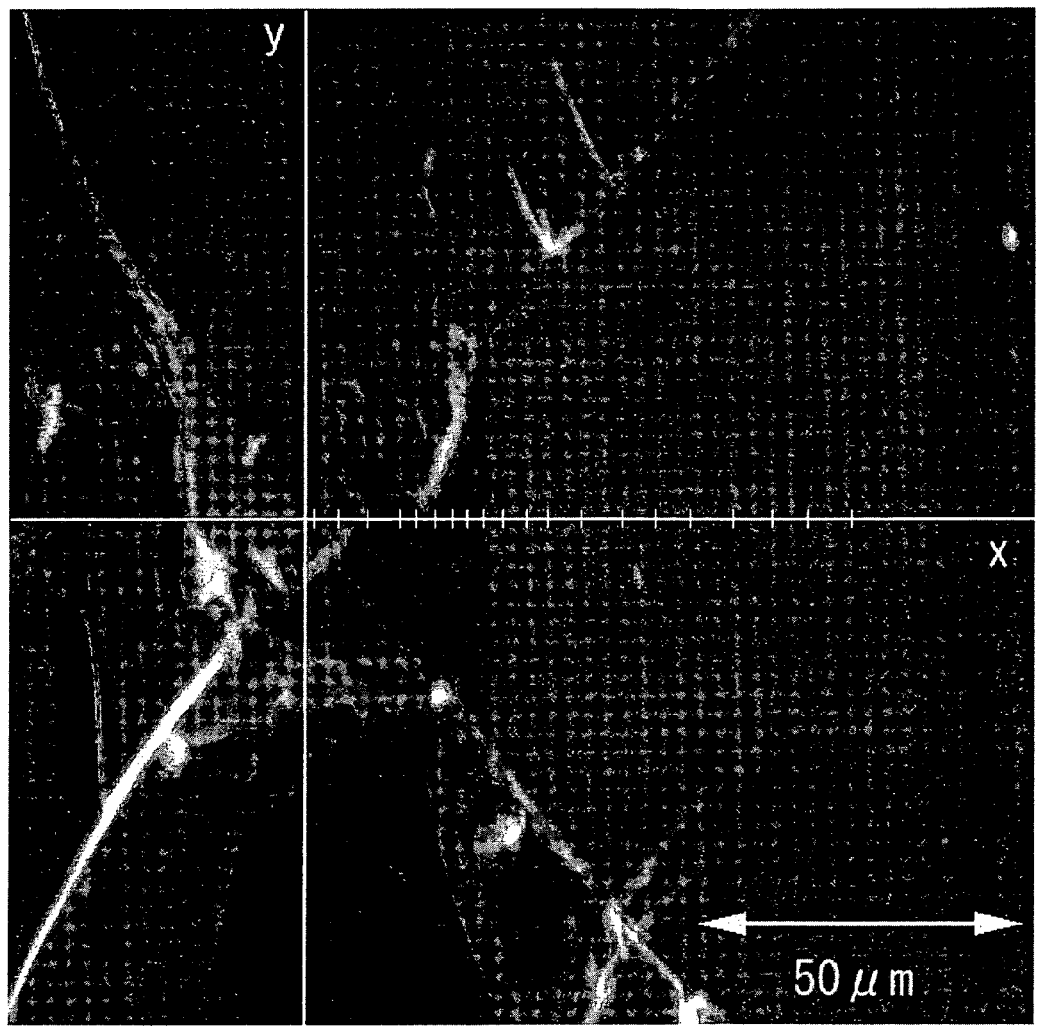
FIG. 10 is an electron microscopic picture of the specimen in accordance with the embodiment 1.
Figure 11:
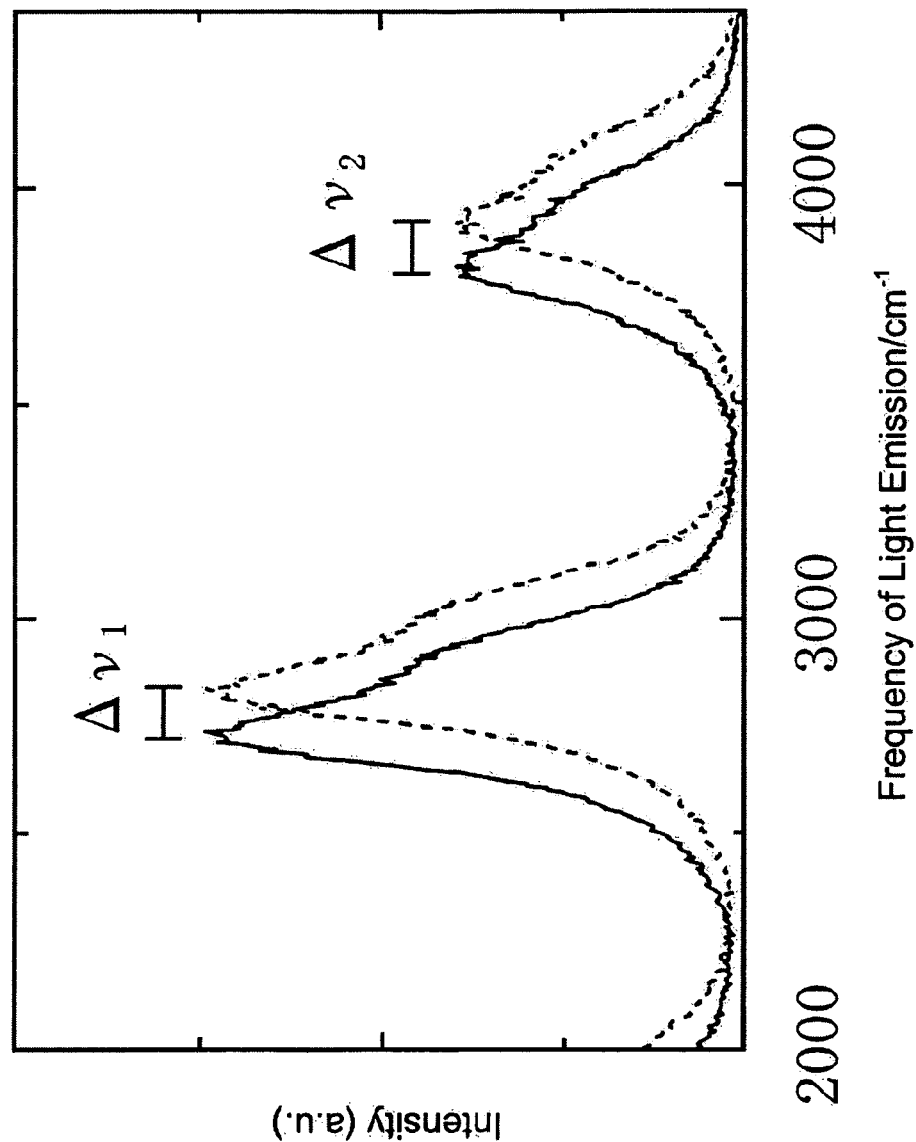
FIG. 11 is a graph showing a contrast between a spectrum in a state that a residual stress exists and a spectrum in a state that no residual stress exists in the embodiment 1.

Next, an indentation (a dent) was made on a surface of the above-mentioned specimen by the use of the external force impressing means as shown in FIG. 10. FIG. 10 is a photo micrograph. Due to this process, a residual stress exists in the specimen. Then spectra of the above-mentioned indentation and its surrounding area were measured under the above-mentioned measuring condition. Contrast between a stress impressed spectrum in a state that a residual stress exists and a specimen spectrum in a state that no residual stress exists is shown in FIG. 11. A solid line in FIG. 11 represents the specimen spectrum and a broken line in FIG. 11 represents the stress impressed spectrum.

Figure 12:
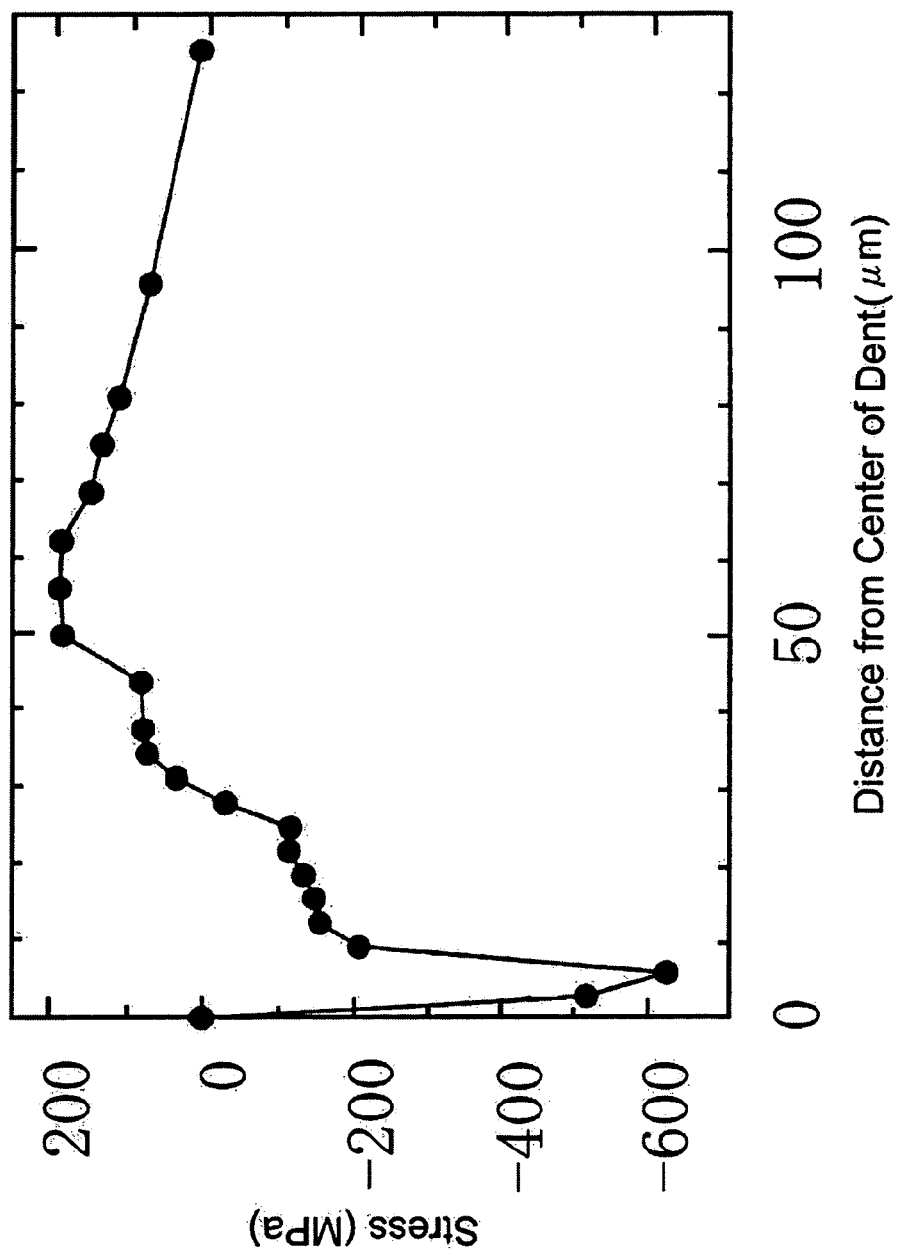
FIG. 12 is a graph showing a measuring result of stress of the specimen in the embodiment 1.

Next, a spectrum shift between the above-mentioned specimen spectrum and the stress impressed spectrum was calculated and a residual stress was calculated based on the correlation of the peak shift to the obtained external force of the specimen. The result is shown in FIG. 12. The calculation of the above-mentioned spectrum shift and the calculation of the residual stress were conducted by the stress calculating means 4.

EXAMPLE FOR COMPARISON

Figure 13:
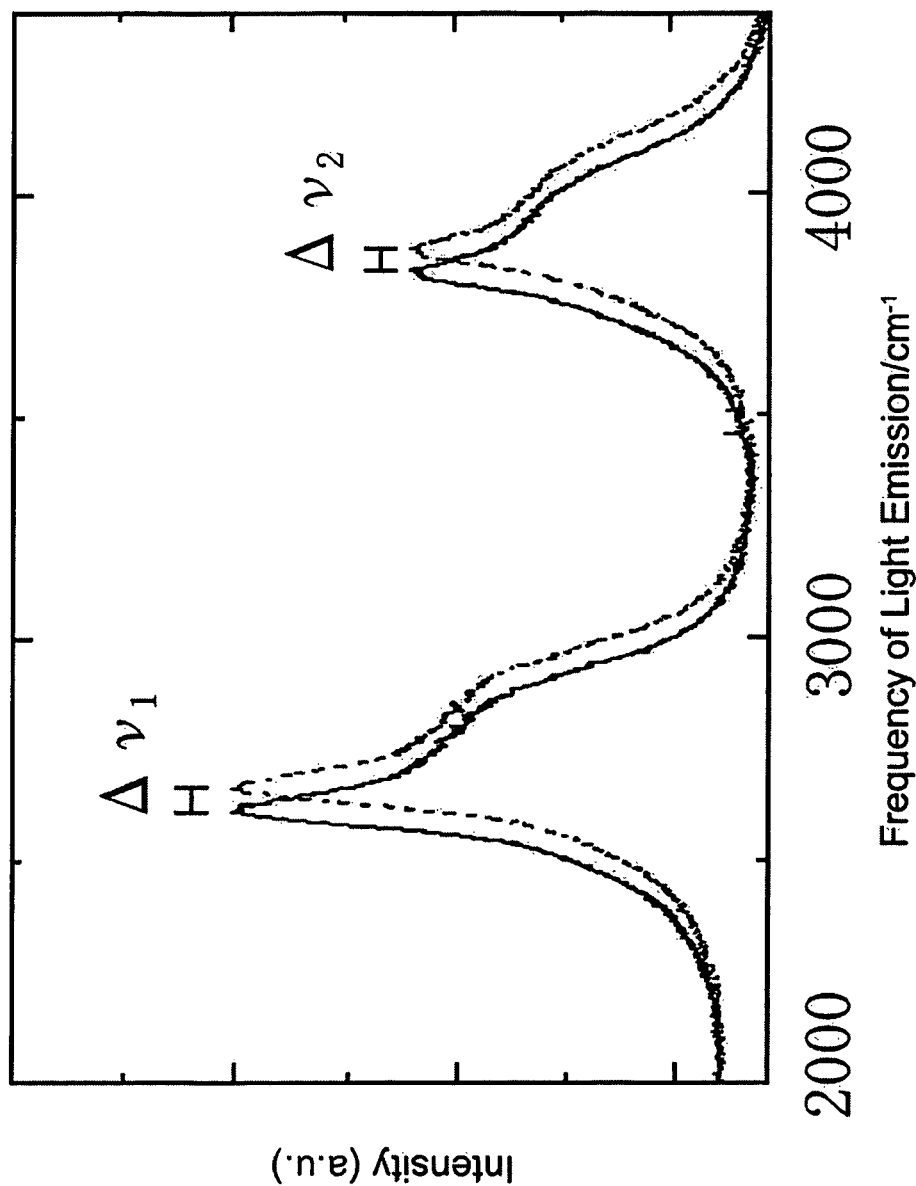
FIG. 13 is a graph showing a contrast between a spectrum in a state that a residual stress exists and a spectrum in a state that no residual stress exists in the comparative example.
Figure 14:
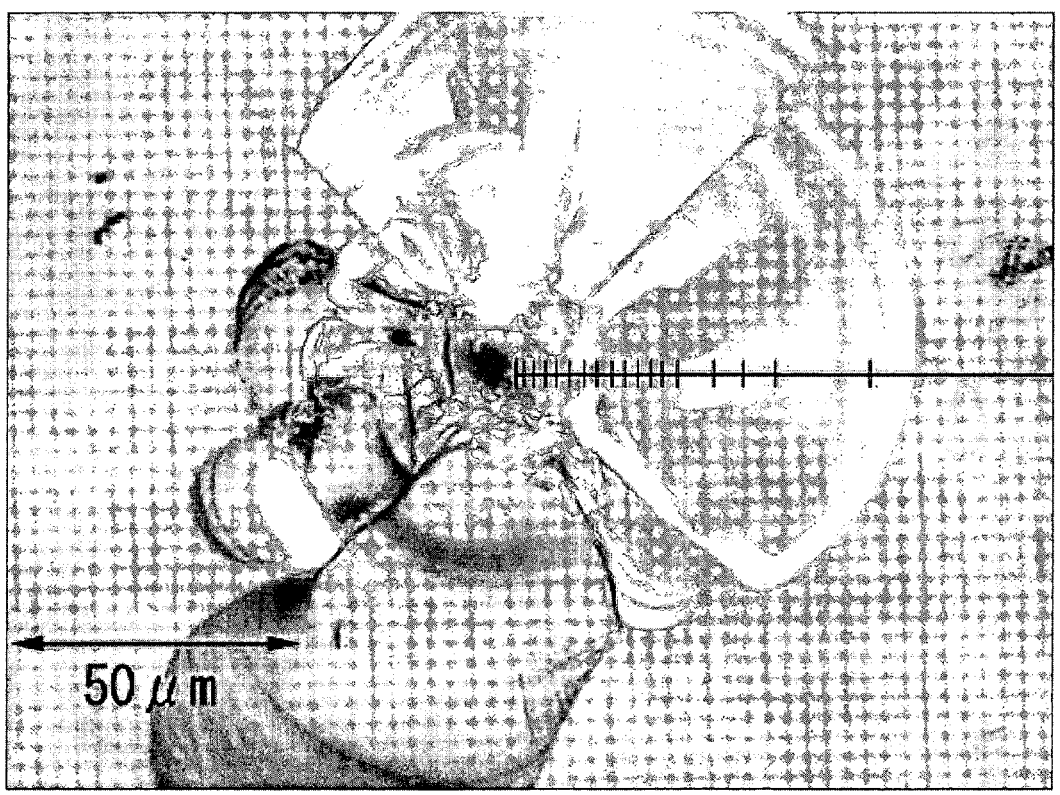
FIG. 14 is an optical microscopic picture of the specimen in the comparative example.
Figure 15:
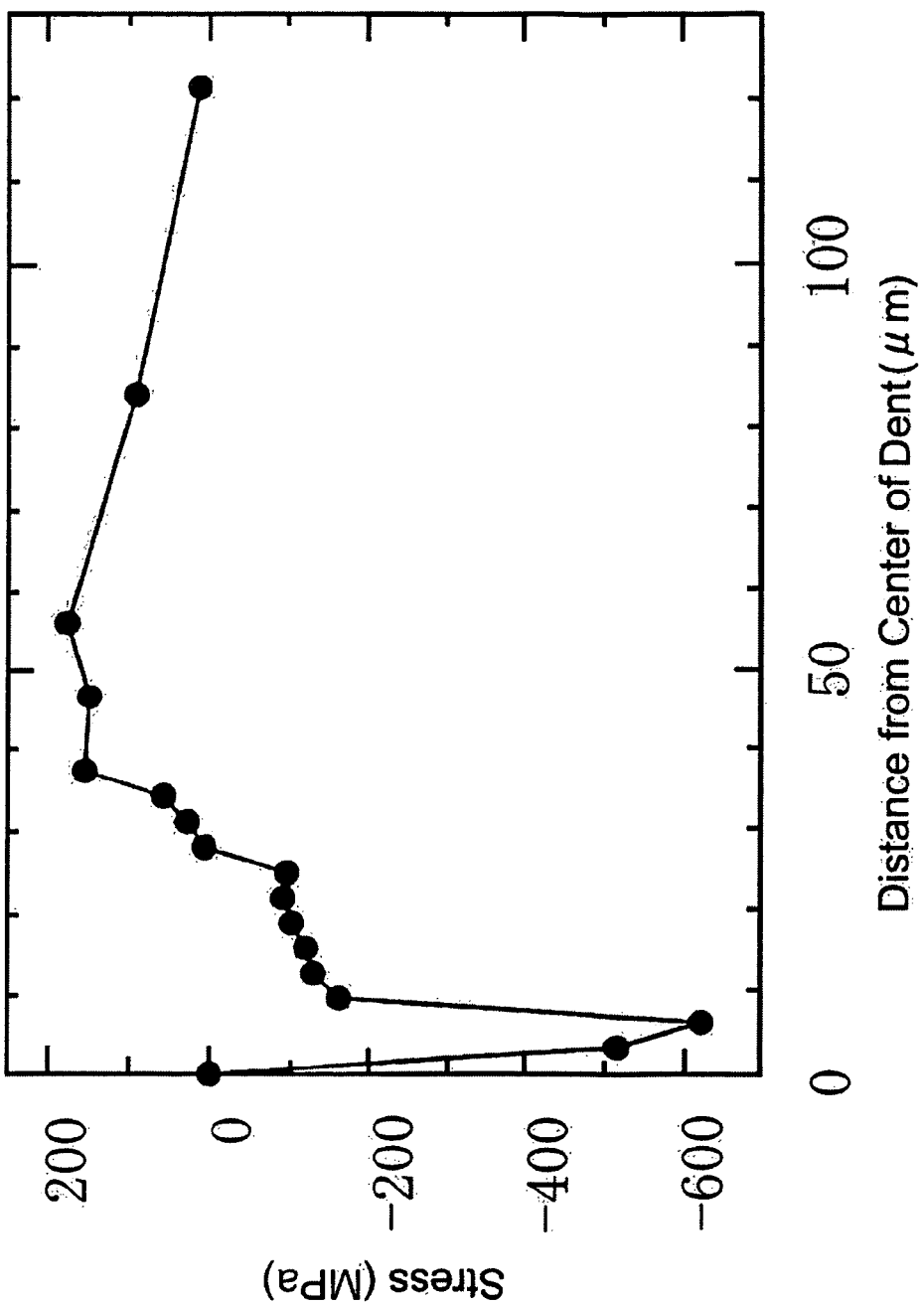
FIG. 15 is a graph showing a measuring result of stress of the specimen in the comparative example.

A correlation of a peak shift to an external force and a spectrum in a state that a residual stress exists and a spectrum in a state that no residual stress exists were obtained by the same operation as that of the embodiment 1 except for using laser light whose beam spot diameter is 1 μm and whose wavelength is 488 nm instead of the electron beam irradiating means 1. The correlation of the peak shift to the external force is shown in FIG. 9. In addition, contrast between a stress impressed spectrum and a specimen spectrum is shown in FIG. 13. A solid line in FIG. 13 represents the specimen spectrum and a broken line in FIG. 13 represents the stress impressed spectrum. An optical electron microscopic picture of the above-mentioned indentation is shown in FIG. 14. Next, a residual stress was calculated based on a spectrum shift between a stress impressed spectrum in a state that the residual stress exists and a specimen spectrum in a state that no residual stress exists and then a residual stress was calculated based on the correlation of the peak shift to the obtained external force of the specimen. The result is shown in FIG. 15.

As mentioned above, as shown in FIG. 12 and FIG. 15, it is understood that a result of the residual stress measured by the use of the laser light and a result of the residual stress measured by the use of the electron beam show the same behavior. Namely, it is understood that the residual stress can be measured also when the electron beam is used.

In addition, as shown in FIG. 9, it is understood that a case of measuring the residual stress by the use of the electron beam is superior in a resolution and the peak shift is more clearly appeared compared with a case of measuring the residual stress by the use of the laser light.

[Embodiment 2]

A stress was measured at three positions in an area of about 90 nm square near a center of the indentation of the specimen measured in the above-mentioned embodiment 1 with making a beam spot diameter of the electron beam 1.5 nm. The beam spot of the above-mentioned 1 μn square becomes about 5 multiplied by 105 spots. The stress was two-dimensionally mapped at any three positions in the 90 nm square. The result is shown in FIG. 16.

Figure 16:
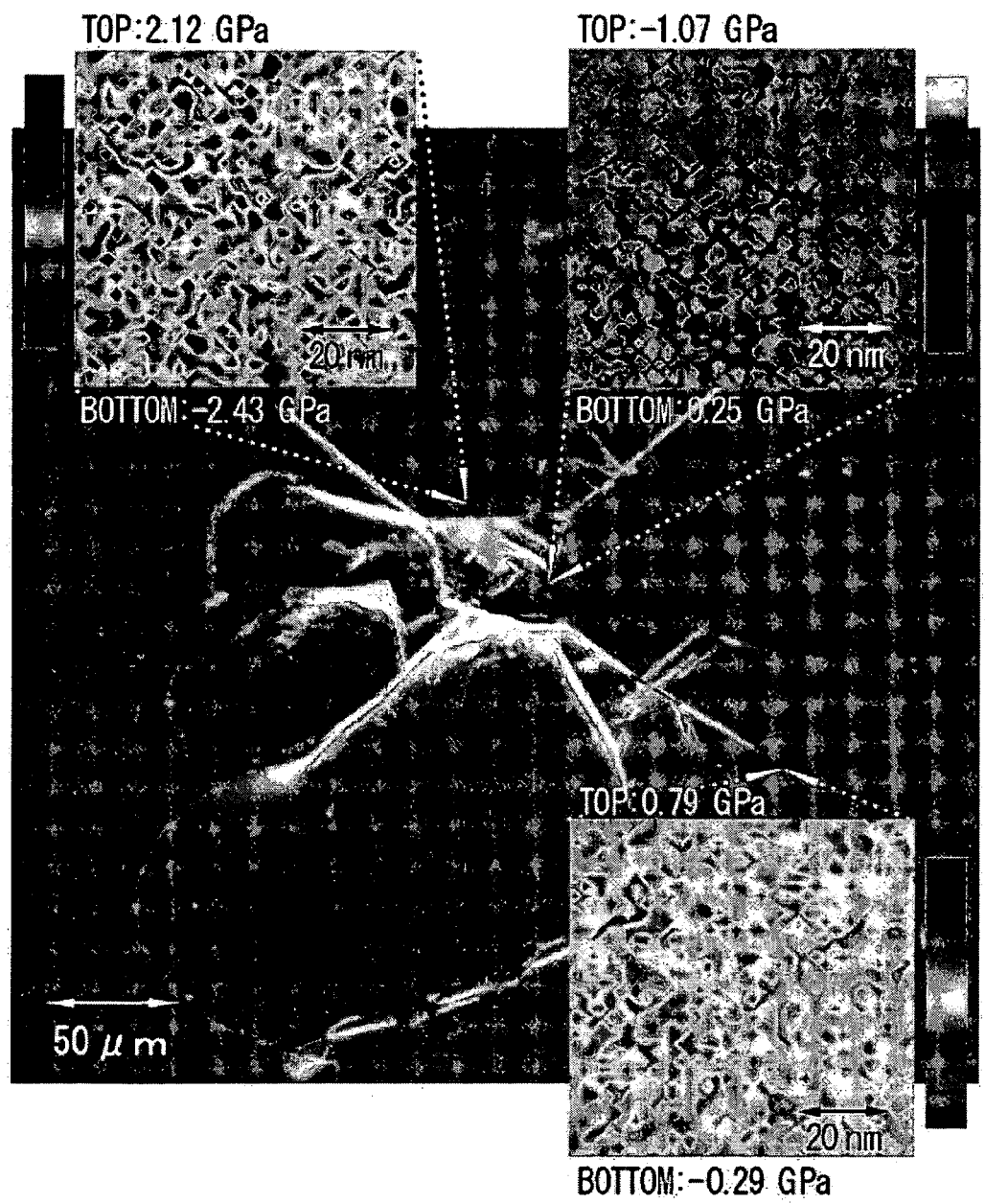
FIG. 16 is a picture showing a stress map wherein a two-dimensional mapping of stress is conducted in an embodiment 2.

As shown in FIG. 16, it is understood that a stress at a microscopic portion varies depending on a position to be measured. It is considered that the unevenness is attribute to a glass structure of a nm scale.

As mentioned above, in the case of measuring the residual stress by the use of the conventional laser light, the diameter of the laser beam spot can be downsized only to an extent of about 1 μm, however, in the case of measuring the residual stress by the use of the electron beam, the diameter of the laser beam spot can be downsized to an extent of 1.5 nm, which makes it possible for the arrangement by the use of the electron beam to improve the positional resolution remarkably.

Possible Applications in Industry

The stress measuring method in accordance with the present claimed invention has an arrangement including a stress calculating process to obtain a stress from a spectrum shift between a specimen spectrum obtained by irradiating the electron beam on the above-mentioned specimen and a stress impressed spectrum of the specimen in a state that a stress exists due to the above-mentioned external force impressing process. As mentioned above, the stress measuring method in accordance with the present claimed invention has an arrangement including the external force impressing process to apply the external force to the specimen, the electron beam irradiating process to irradiate the electron beam on the specimen, the spectroscopy process to obtain the spectrum by conducting the spectroscopy on the light generated from the specimen in the electron beam irradiating process, and the stress calculating process to obtain the stress from the spectrum shift between the specimen spectrum in the state that no stress exists in the specimen and the stress impressed spectrum in the state that the stress exists in the specimen.

In addition, it is preferable that the stress measuring method of this invention further includes an external force impressing process to apply an external force on a specimen prior to the above-mentioned electron beam irradiating process, and the stress calculating means is to obtain a stress from a spectrum shift between an internal stress impressed spectrum in a state that an internal stress is generated in the specimen by the external stress impressing means and the above-mentioned specimen spectrum or the above-mentioned stress impressed spectrum.

As a result, since the diameter of the beam spot can be downsized to an extent not more than 100 nm, more preferably not more than 10 nm, furthermore preferably not more than 2 nm, and the most preferably to an extent of 0.13 nm in case of using the electron beam, it is possible to measure the stress that is extremely high in a positional resolution compared with the conventional method. Since this makes it possible to measure a stress in a high positional resolution (in several nm unit), an effect is produced that a stress can be analyzed in an atom/molecule level regarding to a microscopic portion such as a carbon nanotube or a micro machine whose stress has not been measured by the conventional stress measuring method. A structure of the specimen can also be estimated based on a calculated stress.

It is preferable for the stress measuring method of this invention that external light whose spectrum is known is irradiated in the above-mentioned electron beam irradiating process, a spectrum of the external light and a spectrum of light emission from the specimen are obtained in the above-mentioned spectroscopy process, and each position of spectra of the above-mentioned specimen spectrum and the stress impressed spectrum is compensated based on a spectrum of the external light in the above-mentioned stress calculating process. This makes it possible to minimize an error resulting from a measurement environment, thereby calculating the spectrum shift more accurately.

If the stress measuring method further include a correlation calculating process that calculates a correlation between an amount of the external force impressed on the specimen and an amount of the above-mentioned spectrum shift, it is possible to measure a stress (an internal stress, a residual stress) applied to the specimen in spite of a case that a correlation between an amount of the external force impressed on the specimen and an amount of the above-mentioned spectrum shift is unknown.

It is possible for the stress measuring method of this invention to obtain a clear spectrum if at least one kind of element selected among the lanthanoid is doped by an amount within a range of 1~10000 ppm. In addition, since a very minute amount of the lanthanoid is required to be included in the specimen, it is possible to measure the stress without changing a property (physicality) of the specimen.

In addition, it is preferable that at least one of the elements is selected from the above-mentioned lanthanoid series, especially a family consisting of Sm, Eu, Tb, Y, La, Er, and Gd.

As mentioned above, the stress measuring method has the arrangement comprising the electron beam irradiating means to irradiate the electron beam on the specimen, the spectroscopy means to obtain the spectrum by conducting spectroscopy on the light generated from the spectrum by the electron beam irradiating means, and the stress calculating means to calculate the stress from the spectrum shift between the specimen spectrum in the state that no stress exists in the specimen and the stress impressed spectrum in the state that the stress exists in the specimen.

As a result, it is possible to measure the stress superior in a positional resolution compared with a conventional case using the light generated by irradiating laser light. More concretely, since the diameter of the beam spot can be downsized to an extent not more than 100 nm, more preferably not more than 10 nm, furthermore preferably not more than 2 nm, and the most preferably to an extent of 0.13 nm in case of using the electron beam, it is possible to measure the stress that is extremely high in a positional resolution compared with the conventional method. As a result, an effect is produced that the stress measuring device whose positional resolution is high compared with the conventional stress measuring device can be provided.

The stress measuring device of this invention can measure a stress (an internal stress) in a state that the external force is applied to the specimen by further comprising the external force impressing means that impresses the external force on the specimen.

The stress measuring device of this invention can always measure the stress along a direction of a surface of the specimen and compensate the stress by making use of a reference point when a stress-mapping that displays stress distribution is conducted by further comprising the external light irradiating means that irradiates the external light whose spectrum is known.

The stress measuring device of this invention can indicate a portion to be measured of the specimen accurately by further comprising a visualizing means that visualizes a portion to be measured of the specimen. As a result, it is possible to measure the stress effectively, for example, in case of measuring the stress at the same position.

The stress measuring device of this invention can measure the stress with a higher positional resolution compared with a conventional arrangement of measuring the stress by the use of laser light by making the diameter of the spot of the electron beam irradiated by the above-mentioned electron beam irradiating means not greater than 100 nm, more preferably not greater than 10 nm, furthermore preferably not greater than 1.5 nm, and the most preferably about 0.13 nm.

The stress measuring device of this invention can embody a stress measuring device easily by using a scanning electron microscope as the above-mentioned electron beam irradiating means.

The invention claimed is:

1. A stress measuring device comprising: an electron beam irradiating unit that irradiates a specimen with an electron beam, a spectroscopy unit, operatively configured in association with the electron beam irradiating unit, that is configured to analyze light generated primarily by the electron beam irradiated from the electron beam irradiating unit, and hitting the specimen so as to obtain a spectrum, and a stress calculating unit, operatively configured in association with the spectroscopy unit and the electron beam irradiating unit, that is configured to calculate, from the spectrum of the specimen obtained when the specimen is being irradiated primarily with the electron beam from the electron beam irradiating unit, a stress change generated in the specimen based on a spectrum shift between the spectrum of the generated light obtained when the specimen is in a predetermined state and the spectrum of the generated light obtained when the specimen is in a state different from the predetermined state.

2. The stress measuring device as claimed in claim 1, wherein the stress calculating unit calculates a residual stress where the predetermined state is that where there is no stress in the specimen and the different state is that where there is a residual stress in the specimen.

3. The stress measuring device as claimed in claim 1, further including an external force impressing unit that applies an external force to the specimen which is measured by stress calculating unit.

4. The stress measuring device as claimed in claim 3, wherein the stress calculating unit obtains an internal stress from a spectrum shift between an internal stress impressed spectrum in a state that the internal stress is generated in the specimen by the external stress impressing unit and the specimen spectrum or the stress impressed spectrum.

5. The stress measuring device as claimed in claim 1, further including a composition analyzing unit that analyses a partial difference of composition of the specimen at a measurement site before stress is applied so that the stress calculating unit calculates stress based on the partial difference of composition at the measurement site.

6. The stress measuring device as claimed in claim 1, further including a light irradiating unit that irradiates the specimen with light whose spectrum is known.

7. The stress measuring device as claimed in claim 1, further including a visualizing unit that visualizes a portion to be measured of the specimen so that the portion can be accurately measured again.

8. The stress measuring device as claimed in claim 1, wherein a diameter of a beam spot of the electron beam irradiated by the electron beam irradiating unit is not more than 100 nm.

9. The stress measuring device as claimed in claim 1, wherein the electron beam irradiating unit is a scanning electron microscope.

10. The stress measuring device as claimed in claim 1, further including a light condensing mirror which directs the light generated primarily by the electron beam hitting the specimen to an optical fiber which leads the light to the spectroscopy unit.

11. A system for measuring stress in a specimen with an electron beam comprising: an electron beam irradiating unit that irradiates the specimen with an electron beam; a measuring unit, operatively configured in association with the electron ben irradiating unit, that is configured to provide measurement signals of generated radiation from the specimen and the electron beam from the irradiating unit, primarily by the electron beam radiation; and a calculating unit, operatively configured in association with the measuring unit and the electron beam irradiating unit, that is configured to calculate a stress on the specimen from the measurement signals by determining a spectrum shift between a first spectrum of the generated radiation from the specimen when the specimen is in a predetermined reference state and a second spectrum of the generated radiation from the specimen measured at a predetermined measurement position on the specimen.

12. The system as claimed in claim 11, wherein the calculating unit is adapted to determine the first spectrum of the predetermined reference state by averaging a plurality of measurements across the specimen to approximate a stress-free state for the specimen.

13. The system as claimed in claim 12, wherein the irradiating unit is adapted to direct the electron beam to enable a plurality of measurements representative of an area of the specimen which is approximately 100 times as large or larger than the predetermined measurement position.

14. The system as claimed in claim 11, further including a stress force applying unit wherein the predetermined reference state is determined by measuring the first spectrum with the measuring unit while exerting a stress force on the specimen of a predetermined value with the stress force applying unit and by measuring the second spectrum with the measuring unit at the predetermined measurement position measured without exerting the stress force.

15. The system as claimed in claim 14, wherein the stress force of the stress force applying unit is applied mechanically to the specimen.

16. The system as claimed in claim 14, wherein the stress force of the stress force applying unit is applied thermally to the specimen.

17. The system as claimed in claim 14, wherein the predetermined reference state is measured by the measuring unit over a plurality of different stress forces exerted by the stress force applying unit to correlate the amount of external force and the corresponding spectrum shift.

18. The system as claimed in claim 11, further including a composition analyzing unit that determines the composition of the specimen and that adjusts the calculated stress calculated by the calculating unit on the basis of the determined composition relative to a predetermined composition standard for the specimen.

19. The system as claimed in claim 11, further including a temperature control unit for controlling the temperature of the specimen during the measurement by the measuring unit to a predetermined temperature.

20. The system as claimed in claim 11, further including a light radiating unit that illuminates the specimen with light and a light measuring unit for measuring radiation from the specimen after contact with the light radiation to provide a peak reference for compensation of the electron beam calculated stress by the calculating unit.

21. The system as claimed in claim 11, wherein said irradiating unit irradiates the predetermined measurement position by an electron beam having a diameter of 10 nm or less.

\* \* \* \* \*